(12) United States Patent
Plaskos et al.

(10) Patent No.: US 9,421,019 B2
(45) Date of Patent: *Aug. 23, 2016

(54) ROBOTIC GUIDE ASSEMBLY FOR USE IN COMPUTER-AIDED SURGERY

(75) Inventors: Christopher Plaskos, New York, NY (US); Stephane Lavallee, Saint Martin d'Uriage (FR); Jacques Rit, Monte Carlo (MC)

(73) Assignee: OMNilife science, Inc., Raynham, MA (US)

( * ) Notice: Subject to any disclaimer, the term of this patent is extended or adjusted under 35 U.S.C. 154(b) by 813 days.

This patent is subject to a terminal disclaimer.

(21) Appl. No.: 11/908,449

(22) PCT Filed: Apr. 7, 2006

(86) PCT No.: PCT/IB2006/000806
§ 371 (c)(1),
(2), (4) Date: Aug. 10, 2010

(87) PCT Pub. No.: WO2006/106419
PCT Pub. Date: Oct. 12, 2006

(65) Prior Publication Data
US 2011/0130761 A1   Jun. 2, 2011

Related U.S. Application Data

(60) Provisional application No. 60/669,177, filed on Apr. 7, 2005.

(51) Int. Cl.
*A61B 17/15* (2006.01)
*A61B 17/16* (2006.01)

(52) U.S. Cl.
CPC ............... *A61B 17/155* (2013.01); *A61B 90/36* (2016.02); *A61B 17/1675* (2013.01); *A61B 2017/1602* (2013.01); *A61B 2034/2055* (2016.02); *A61B 2034/2068* (2016.02)

(58) Field of Classification Search
CPC ...................................................... A61B 34/30
USPC ......... 606/88, 130, 79, 80, 81, 82, 83, 84, 85, 606/86 R, 87, 96, 97, 98
See application file for complete search history.

(56) References Cited

U.S. PATENT DOCUMENTS 3,987,498 A * 10/1976 Mason .................... A61F 2/582
623/24
4,457,307 A    7/1984 Stillwell
(Continued)

FOREIGN PATENT DOCUMENTS

CA    2219190    11/1996
CA    2376019    1/2001
(Continued)

OTHER PUBLICATIONS

Office Action issued Feb. 27, 2009 in U.S. Appl. No. 11/305,887.
(Continued)

*Primary Examiner* — Samuel Hanna
(74) *Attorney, Agent, or Firm* — Kim Winston LLP

(57) ABSTRACT

A system for guiding resurfacing operations on at least a portion of a joint of at least one bone is provided and uses a guide with actuators (motors) controlled by a computer to position a cutting tool relative to a bone so that the bone surface can be cut in a flexible and accurate manner.

31 Claims, 21 Drawing Sheets

(56) References Cited

U.S. PATENT DOCUMENTS

| | | |
|---|---|---|
| 4,574,794 A | 3/1986 | Cooke et al. |
| 5,228,459 A | 7/1993 | Caspari et al. |
| 5,417,695 A | 5/1995 | Axelson, Jr. |
| 5,454,816 A | 10/1995 | Ashby |
| 5,474,559 A | 12/1995 | Bertin et al. |
| 5,571,110 A | 11/1996 | Matsen et al. |
| 5,601,563 A | 2/1997 | Burke et al. |
| 5,624,440 A * | 4/1997 | Huebner .................. 606/59 |
| 5,653,714 A | 8/1997 | Dietz et al. |
| 5,682,886 A | 11/1997 | Delp et al. |
| 5,683,397 A | 11/1997 | Vendrely et al. |
| 5,710,870 A | 1/1998 | Ohm et al. |
| 5,769,855 A | 6/1998 | Bertin et al. |
| 5,806,518 A | 9/1998 | Mittelstadt |
| 5,817,097 A | 10/1998 | Howard et al. |
| 5,824,085 A | 10/1998 | Sahay et al. |
| 5,860,981 A | 1/1999 | Bertin et al. |
| 5,916,231 A | 6/1999 | Bays |
| 6,056,754 A | 5/2000 | Haines et al. |
| 6,132,368 A | 10/2000 | Cooper |
| 6,226,548 B1 | 5/2001 | Foley et al. |
| 6,527,443 B1 | 3/2003 | Vilsmeier et al. |
| 6,554,837 B1 * | 4/2003 | Hauri ............ A61B 17/154 606/87 |
| 6,558,391 B2 | 5/2003 | Axelson, Jr. et al. |
| 6,575,980 B1 | 6/2003 | Robie et al. |
| 6,685,711 B2 | 2/2004 | Axelson, Jr. et al. |
| 6,702,821 B2 | 3/2004 | Bonutti |
| 6,712,824 B2 | 3/2004 | Millard et al. |
| 6,738,656 B1 | 5/2004 | Ferre et al. |
| 6,858,032 B2 | 2/2005 | Chow et al. |
| 7,029,477 B2 | 4/2006 | Grimm |
| 7,488,324 B1 | 2/2009 | Metzger et al. |
| 7,520,880 B2 | 4/2009 | Claypool et al. |
| 7,547,307 B2 | 6/2009 | Carson et al. |
| 7,569,060 B2 | 8/2009 | Faoro |
| 8,096,997 B2 | 1/2012 | Plaskos et al. |
| 8,126,533 B2 | 2/2012 | Lavallee |
| 8,282,646 B2 | 10/2012 | Schoenefeld et al. |
| 8,545,509 B2 | 10/2013 | Park et al. |
| 8,617,171 B2 | 12/2013 | Park et al. |
| 2004/0039396 A1 | 2/2004 | Couture et al. |
| 2004/0127788 A1 | 7/2004 | Arata |
| 2004/0172138 A1 * | 9/2004 | May et al. .................. 623/20.36 |
| 2004/0221625 A1 | 11/2004 | Aouad |
| 2005/0055028 A1 * | 3/2005 | Haines ............ A61B 17/155 606/79 |
| 2005/0101966 A1 | 5/2005 | Lavallee |
| 2005/0149041 A1 * | 7/2005 | McGinley ........ A61B 17/155 606/88 |
| 2005/0234435 A1 | 10/2005 | Layer |
| 2006/0015114 A1 | 1/2006 | Bernardoni et al. |
| 2006/0052791 A1 | 3/2006 | Hagen et al. |
| 2006/0161052 A1 | 7/2006 | Colombet et al. |
| 2006/0200161 A1 | 9/2006 | Plaskos et al. |
| 2007/0106128 A1 | 5/2007 | Lavallee |
| 2007/0185498 A2 | 8/2007 | Lavallee |
| 2008/0004481 A1 | 1/2008 | Bax et al. |
| 2008/0243127 A1 | 10/2008 | Lang et al. |
| 2009/0018445 A1 | 1/2009 | Schers et al. |
| 2009/0024142 A1 | 1/2009 | Ruiz Morales |
| 2009/0228016 A1 | 9/2009 | Alvarez |
| 2010/0130986 A1 | 5/2010 | Mailloux et al. |
| 2010/0256504 A1 | 10/2010 | Moreau-Gaudry et al. |
| 2010/0268240 A1 * | 10/2010 | McGinley et al. .............. 606/88 |
| 2011/0029091 A1 | 2/2011 | Bojarski et al. |
| 2011/0071530 A1 | 3/2011 | Carson |
| 2011/0087332 A1 | 4/2011 | Bojarski et al. |
| 2011/0130761 A1 | 6/2011 | Plaskos et al. |

FOREIGN PATENT DOCUMENTS

| | | | |
|---|---|---|---|
| DE | 203036643 U1 | 2/2003 | |
| FR | WO2004/112620 A1 * | 6/2004 | ............ A61B 17/15 |
| FR | 2856268 A1 | 12/2004 | |
| WO | 9832384 A1 | 7/1998 | |
| WO | 9960939 | 12/1999 | |
| WO | 2004/112620 A1 | 12/2004 | |
| WO | 2006106419 A2 | 10/2006 | |

OTHER PUBLICATIONS

Office Action issued Nov. 13, 2009 in U.S. Appl. No. 11/305,887.
Int'l Search Report issued Sep. 29, 2006 in Int'l Application No. PCT/IB2006/000806; Written Opinion.
Int'l Preliminary Report on Patentability issued Oct. 9, 2007 in Int'l Application No. PCT/IB2006/000806; Written Opinion.
"Building a complete surface model from sparse data using statistical shape models: application to computer assisted knee surgery" by M. Fleute and S. Lavallée, published in Medical Image Computing and Computer-Assisted Intervention—MICCAI'98, Spinger-Verlag LNCS Series, pp. 880-887, Oct. 1998.
Fleute M, Lavallee S, Julliard R. Incorporating a statistically based shape model into a system for computer-assisted anterior cruciate ligament surgery. Medical Image Analysis. Sep. 1999; 3(3):209-22.
Cobb J, Henckel J, Gomes P, et al, Hands-on robotic unicompartmental knee replacement, Journal of Bone and Joint Surgery—British vol., 2006, vol. 88, pp. 188-197, ISSN: 0301-620X.
Jakopec M, Harris SJ, Rodriguez y Baena F, et al, The first clinical application of a 'Hands-On' robotic knee surgery system, Computer Aided Surgery, 2001, vol. 6, pp. 329-339, ISSN: 1092-9088.
U.S. Office Action issued Oct. 16, 2012 in U.S. Appl. No. 12/616,575.
Office Action issued Jul. 29, 2013 in U.S. Appl. No. 12/616,575.
Office Action issued Mar. 26, 2014 in U.S. Appl. No. 12/616,575.
Office Action issued Sep. 9, 2014 in U.S. Appl. No. 13/524,424.
Office Action dated Apr. 10, 2015 in U.S. Appl. No. 13/524,424.

* cited by examiner

ROBOTIC GUIDE ASSEMBLY FOR USE IN COMPUTER-AIDED SURGERY

CROSS REFERENCE TO RELATED APPLICATION

This is a U.S. National Phase application under 35 U.S.C. §371 of International Application No. PCT/IB2006/000806, filed on Apr. 7, 2006, and claims the benefit of U.S. patent application Ser. No. 60/669,177, filed Apr. 7, 2006, both of which are hereby incorporated by reference in their entirety.

TECHNICAL FIELD

The present invention relates to a method and system for computer and robot aided surgery and more particularly, relates to a robot-aided guide assembly that has a guide mechanism and cutting tool for making precise bone cuts as part of a surgical procedure, such as joint replacement or resurfacing operations.

BACKGROUND

The World Health Organization estimates that there is currently several hundreds of millions of people suffering from bone and joint diseases, and this figure is projected to increase sharply due to the predicted doubling of the number of people over 50 by the year 2020.

Partial or total joint replacement or resurfacing is currently one of the most popular methods of treating for patients who suffer from bone and joint diseases, such as severe degenerative joint osteoarthritis or arthrosis. For instance, approximately 600,000 osetoarthritis patients worldwide undergo total knee arthroplasty (TKA) every year to relieve their joint pain and to restore their proper knee function with respect to joint loading and kinematics. Uni-compartmental knee arthroplasty (UKA), where only the medial or lateral condyles of the femur and tibia are replaced is also a popular and is a less invasive treatment for certain patients with knee osteoarthritis.

There are several different surgical techniques and forms of implants used for both TKA and UKA. In conventional TKA, for example, the surgeon strives to achieve accurate alignment by adequately exposing the knee joint, properly orientating cutting guide blocks across the exposed aspect of the bones from the anterior side of the knee, and sawing off the worn joint surface by using the block surface or slot to guide the oscillating saw-blade.

To adequately expose the knee joint, the standard approach used is a 25-30 cm skin incision extending proximally from just distal to the level of the tibia tubercle (known as the anterior or midline approach), followed by a medial 20-30 cm parapatellar arthrotomy, which extends superiorly through the quadriceps tendon. Although the extent of the incision allows for lateral evertion and dislocation of the patella, thus exposing most of the structures of the knee joint, dividing the distal third of the quadriceps muscle in this manner can have several potential repercussions for the patient. These include increased pain, blood loss, and time to ambulation (both with and without walking aids), prolonged post-operative hospital stay and rehabilitation, and decreased range of motion and knee strength in daily tasks, such as stair climbing and descending stairs, etc.

Minimally invasive surgical (MIS) techniques have been used only for uni-condylar knee arthroplasty for over a decade, though surgeons have only relatively recently begun to apply the principles of MIS to TKA. In this technique, the knee joint is accessed mainly from the side through a 6-9 cm incision instead of a 20-30 cm incision. Approaching bone cuts medially or obliquely instead of anteriorly circumvents the need to evert the patella and violate the quadriceps. This, in turn, reduces morbidity by reducing the trauma to the extensor mechanism, and improves post-operative knee function, recovery rate and pain.

In TKA, implant alignment and positioning is regarded to be one of the most important surgical variables for the long term success of the operation. Implant alignment and positioning can be described by the degrees of freedom associated with each implant. For the femoral component these include three rotations, namely, varus/valgus alignment, flexion/extension alignment, and internal/external or transverse alignment; as well as three positions, namely, anterior-posterior (AP) positioning, proximal-distal (PD) positioning and medial-lateral (ML) positioning. Most TKA femoral implants include an inner surface comprised of at least five planes. The five cutting planes that must be realized on the distal femur are the interior cut, anterior chamfer cut, distal cut, posterior chamfer cut and posterior cut. Other inner implant geometries consist of curved surfaces.

In order to accommodate these different surgical techniques and implants, there exists several different types of bone-cutting or resurfacing guides. These can range from rigid mechanical jigs, to mechanized systems, to robotic cutting guides. Some of these conventional guides are disclosed in U.S. Pat. Nos. 6,858,032 and 5,228,459; U.S. application publication No. 2005/0055028 and German patent No. DE 203036643, all of which are hereby incorporated by reference in their entireties.

Most of the above conventional systems use some type of template to guide a cutting tool. However, all of these conventional systems suffer from a number of deficiencies and in particular, these systems do not provide all of the following desired features: accuracy with respect to global implant positioning; accuracy with respect to bone cut surface reproducibility; flexibility in terms of implant type; flexibility in terms of inner implant surface complexity, geometry and size; compatibility with minimal access approaches; compactness; simplicity and ease-of use.

SUMMARY

The present invention relates to a system for guiding resurfacing operations on at least a portion of a joint of at least one bone. The system uses a guide with actuators (motors) controlled by a computer to position a cutting tool relative to a bone so that the bone surface can be cut in a flexible and accurate manner.

The system of the present invention includes a number of components that cooperate with one another to perform the intended guide and cutting operations. In particular, the system can include fixation instrumentation, an orienting apparatus, a positioning mechanism, and a guide assembly for guiding a cutting or milling tool.

According to one embodiment, a system for guiding a cutting tool capable of cutting bone portions at a level of a head of a bone is provided and includes (a) means for attaching the system to only one side of the bone through an incision in the bone; (b) an adjustment mechanism rotatably coupled to the attachment means for adjusting the position of the cutting tool; (c) a positioning mechanism coupled to the adjustment mechanism and having at least two degrees of rotational freedom for further adjusting the position of the cutting tool; and (d) a guide intended to support the cutting tool and pivotally coupled to the positioning mechanism along one axis of rotation of the positioning mechanism.

These and other features and aspects of the invention can be appreciated from the accompanying figures and the following description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which:

FIG. 4b is a side elevation view, in cross-section, of a variation of the fixation instrument of FIG. 4a.

FIG. 7 is an exploded perspective view of a pin guide and anchor of the fixation instrument of FIG. 4a;

DETAILED DESCRIPTION OF PREFERRED EMBODIMENTS

Figure 1:
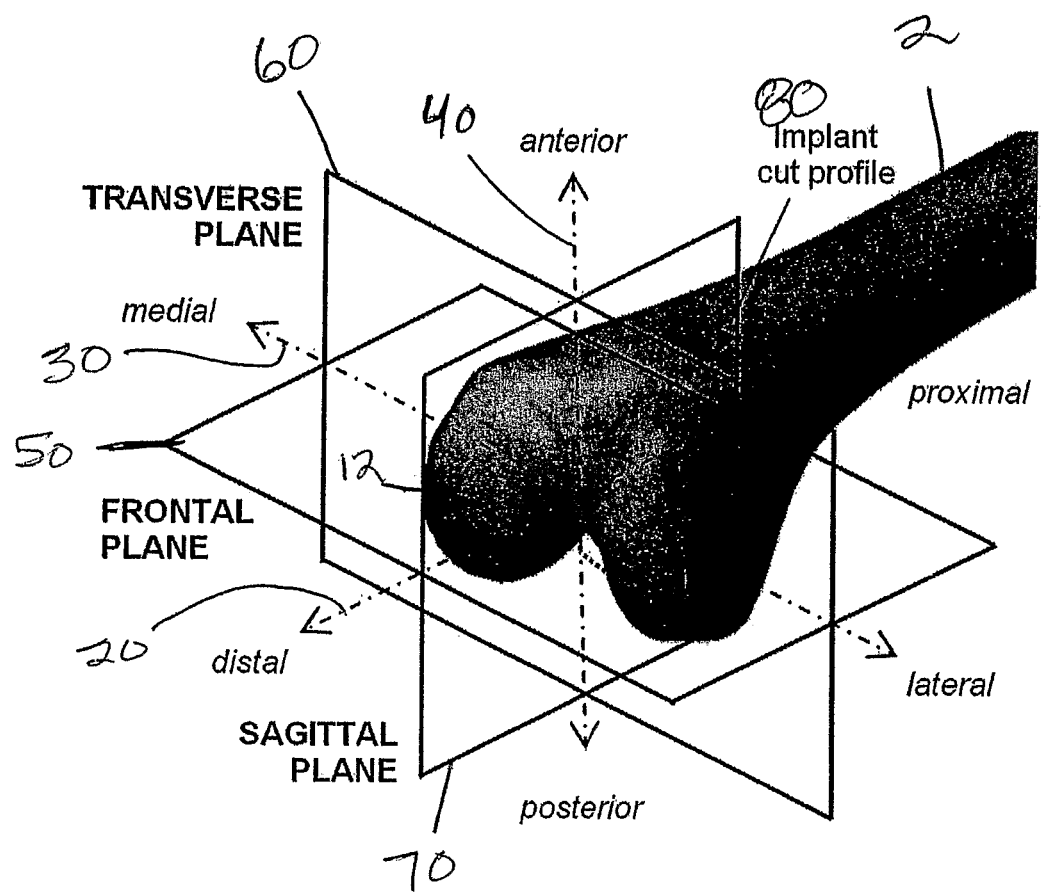
FIG. 1 is a perspective view of an anatomical coordinate system of a knee.

Referring now to FIG. 1, a perspective anatomical coordinate system of the knee is illustrated. More specifically, a bone 2 (e.g., femur) is shown and includes a distal end 12. A proximal/distal axis 20 is provided to show proximal and distal directions relative to the femur 2. In addition, a medial/lateral axis 30 is provided to show the medial and lateral portions of the femur 2 and an anterior/posterior axis 40 is provided to show the anterior and posterior portions of the femur 2. To assist in performing resurfacing and cutting operations on the femur 2, several reference planes are provided. In particular, a frontal plane 50 is provided, a transverse plane 60 is provided, and a sagittal plane 70 is provided. For purpose of illustration only, an implant cut profile 80 is illustrated and projected onto the sagittal plane 70 to illustrate the five planar cuts of a typical total knee arthroplasty (TKA) femoral implant.

Figure 2:
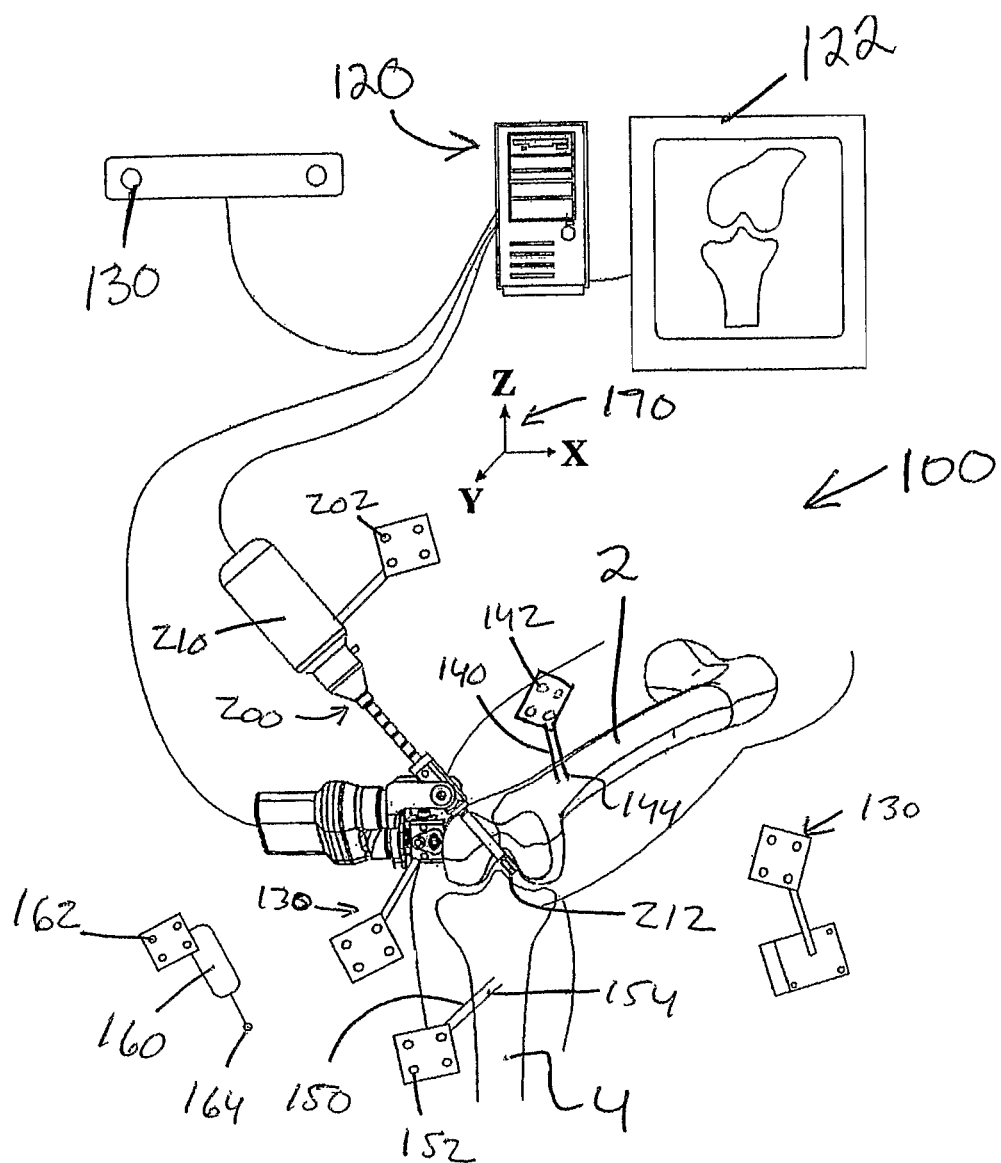
FIG. 2 is a perspective view of a computer and robot assisted surgery system.

Referring now to FIG. 2, a computer-assisted orthopedic surgery (CAOS) system 100 is schematically shown. The system 100 is configured for performing joint replacement or resurfacing operations, such as TKA. The system 100 can be used to plan the optimal position of an implant, such as a knee implant, relative to the bone 2, 3, and to position a guiding system such that the final cut surface corresponds to the planned implant position cut surface.

The system 100 includes a suitable position measuring device 110 that can accurately measure the position of marking elements in three dimensional space and in the case of a knee implant, the device 110 includes at least one bone, such as the patient's femur 2 or tibia 4. The position measuring device 110 can employ any type of position measuring method as may be known in the art, for example, emitter/detector or reflector systems including optic, acoustic or other wave forms, shape based recognition tracking algorithms, or video-based, mechanical, electromagnetic and radio frequency systems. In a preferred embodiment, schematically shown in FIG. 2, the position measuring system 110 is an optical tracking system that includes at least one camera that is in communication with a computer system 120 and positioned to detect light reflected from a number of special light reflecting markers, such as spheres or discs 130. The computer system 120 includes a display 122 to permit visual display of the images.

Detecting and determining the position and orientation of an object is referred to herein as "tracking" the object. To provide precision tracking of objects, markers 130 can be rigidly connected together to form reference bodies, (e.g., 140, 150), and these reference bodies can be attached to bones, tools and other objects to be tracked. One such device that has been found to be suitable for performing the tracking function is the Polaris™ system from Northern Digital Inc., Ontario, Canada. Objects to be tracked thus typically include at least three markers (or triplets), which can be configured to emit, receive, or reflect energy, such as light or acoustic energy.

The position measurement device 110 is described in greater detail in a number of publication, including U.S. patent application Nos. 20050101966 and 11/299,287, both of which were previously incorporated by reference.

To sense the position of light reflecting markers, the system 100 includes at least two detecting elements, such as two cameras. The two cameras detect the light reflected from the light reflecting markers to determine the position of each marker associated with the tracked object, the position and orientation of the tracked object are also determined.

The position of the patient's bones, such as the patient's femur 2 and the patient's tibia 4, can be determined and tracked by attaching reference bodies 140, 150, which include respective markers 142, 152. Reference bodies can be attached to bones or tools using pins or screws (144, 154), or various quick release mechanisms. The reference bodies can also be shaped in the form numbers (e.g., "1", "2", "3" . . . ) or alphabetical letters, such as "F" for Femur, "T" for Tibia, "P" for pointer, and so on, so as to avoid confusion as to which reference body should be attached to which bone or tool.

The tracked objects and there relative positions can be displayed on a screen that is connected to the computer system 120. In a preferred embodiment, the display is a touch screen which can also be used for data entry.

The position measurement device 110 includes a number of different tools that are used at different locations and perform different functions as the system 100 is operated to yield optimal joint reconstruction data and information. These tools include the above described markers, which act as landmark markers, as well as other tools as will described in greater detail below, such as a milling or cutting system 200 having at least three markers 202 is an example of an object trackable by position measuring device 110. The system also includes a pointer 160, with markers 162, which can be used to digitize points on the surfaces of the femur 2 and tibia 4. The system 100 can further include a calibration device that can be used to measure the relationship between a pointer tip 164 and the markers 162. Accordingly, the markers 162 permit the position or the pointer tip 164 to be determined from the positions of the markers 162 relative to the three-dimensional coordinate system 170.

For sake of simplicity and with respect to the discussion of FIG. 2, the system 200 is described as including a milling or drilling device or any other type of cutting device 210 also has a tip 212 having a known spatial relationship relative to markers 202. Position measuring device 110 determines the position and orientation of markers 202 in the three dimensional coordinate system 170. Based upon the known spatial relationship between the tip 212 and markers 202, the position of the tip 212 is determined.

Computer 120 is optionally configured to allow at least one of medical image data and ultrasound data to be used in planning the position and orientation of an implant in a bone. The trajectory or path of a cutting surface being milled by the device 210 can be monitored and displayed by the computer 120. Thus, the actual path can be compared to the previously planned cut path to allow the practitioner to verify that there is no deviation between the actual procedure and the preoperative plan. In one embodiment, the device 210 is guided to allow the computer 120 to control the milling or drilling path.

The system 100 also includes a plurality of reference bodies 140, 150, for determining the position and orientation of an individual's bone in the three dimensional coordinate system 170. The reference bodies 140, 150 are preferably rigid and include respective markers 142, 152, which are preferably configured to emit or reflect energy. Each reference body 140, 150 preferably includes a respective attachment element, such as pins or screws 144, 154, with which the reference bodies can be releasably attached to a bone. For example, the reference body 140 can be attached to femur 2. The position and orientation of femur 2 can be determined based upon the position and orientation of markers 142 attached thereto.

Markers 142, 152 are sufficient to establish the position and orientation of the rigid bodies 140, 150 within the coordinate system 170.

The system 100 also includes the pointer 160 and can include an endoscope in some applications, which cooperate to allow a practitioner to digitize landmarks of the femur 2 and tibia 4. Digitizing a landmark comprises determining the position of the landmark in the three dimensional coordinate system, as discussed below. The pointer 160 preferably includes a pointer tip 164 having a known spatial relationship to the markers 162. Based upon the known spatial relationship, the position of the pointer tip 164 can be determined from the position and orientation of the markers 162.

The system 100 can further include a planar probe that includes at least one planar surface for measuring the position and orientation of the planar probe to be determined. Moreover, a calibration system is preferably provided to measure the relationship between at least one of the planar surfaces on the probe and the markers. This relationship can also be determined by using the pointer 160 to point to and locate at least three points on the planar surface. Alternatively, the three points can have any known spatial relationship relative to the planar surface. Thus, the position of the planar surface can be determined from the positions of the markers relative to the three-dimensional coordinate system 170. In addition, other planar surfaces can be in a known relative position with respect to the calibrated planar surface or the three or more located points.

In a preferred embodiment of the invention landmark points and or directions are digitized with respect to the femur 2 and tibia 4 with the pointer and are stored in the computer. Preferably an anatomical coordinate system for the femur and the tibia is defined based on at least a portion of the acquired data. The coordinate system could also be defined at least partially using kinematic methods, such as fitting a plane to a trajectory (e.g. fitting the sagittal plane 70 to the flexion/extension trajectory). Possible landmark points include but are not limited to the tibial plateau glenoids, spine, malleoli, the femoral notch, condyles, hip center, bone surface areas, etc.

Now referring to FIGS. 2-20, the surgical system 100 is preferably an integrated system in which each of the tools is in communication with a master controller, such as the computer 120, which serves to collect all of the data from the individual tools and then process the data to calculate various measurements that are displayable to the physician. The system 100 accordingly includes a user interface that is supported by software in the computer 120. The user interface is configured to assist and walk the physician through the surgical procedure(s) to obtain optimal results and to assist the physician in determining what the best course of action is in terms of performing joint resurfacing and bone cutting operations.

To perform computer assisted orthopedic surgery, especially joint replacement or resurfacing, using the present system 10, the reference body 140 is attached to the femur 2 at a selected point, as by screwing the reference body 140 into the bone with screws 144. The reference body 140 includes the first set or triplet of markers 142 that are thus fixed to the femur 2 at the point. Similarly, the reference body 150 is attached to the tibia 4 at a selected point by screwing the body 150 into the bone with screw 154. The reference body 150 includes the second set or triplet of markers 152 that are likewise fixed to the tibia 4. Since the reference bodies 140, 150 are fixed to the bones 2, 4, the pointer tip 164 can be used to point at any given point on bone 2, 4, the position of which is precisely taken by its tip 164. Then, it is possible using a conventional data processing system to determine the vector connecting the point where the respective body 140, 150 attaches to the bone 2, 4 to the point of the tip 164, and therefore, locate any given point for any position of the femur 2 or tibia 4.

According to one exemplary method, a number of different reference points are obtained. For example, the pointer tip 164 is used to digitize certain surfaces of the tibia 4. Acquisition or data points are also taken for the femur bone 2 and more particularly, the pointer 160 is moved along the distal surfaces of the femur bone 2. In all of these steps, the digitization occurs by locating and logging a selected bone surface point in the three dimensional coordinate system 170 and by using the data processing system. In other words, the pointer tip 164 is moved along the bone surface and coordinate data are gathered for use in generating a morphological model of that bone portion. The pointer 160 can be actuated to begin data acquisition by simply activating an actuator, such as a foot pedal in which case it is merely depressed by the physician. The above described digitizing process can be thought of as a landmark acquisition process. Thus, according to a preferred embodiment of the present invention, landmark points and/or directions are digitized with respect to the femur 2 and the tibia 4 utilizing the pointer 160 and are stored in the computer 120. Preferably, an anatomical coordinate system for the femur 2 and the tibia 4 is defined based on at least a portion of the acquired data. The coordinate system can also be defined at least partially using kinematic methods, such as fitting a plane to a trajectory (e.g., fitting the sagittal plane to the flexion/extension trajectory). As discussed in some detail above, possible landmark points include but are not limited to the tibial plateau glenoids, spine, malleoli, the femoral notch, condyles, hip center, bone surface areas, etc. The data acquisition points can be used to determine other information, such as locating a mechanical axis of the tibia 4.

In a preferred embodiment of the present invention, three dimensional geometrical surface models of the bones are provided by image-free means. Preferably these models are obtained by adjusting a deformable model of the bone to points acquired on the bone surface. Examples of some known methods of carrying out this task can be found in the following references: (1) "Building a complete surface model from sparse data using statistical shape models: application to computer assisted knee surgery" by M. Fleute and S. Lavallee, published in Medical Image Computing And Computer-Assisted Intervention—MICCAI'98, Spinger-Verlag LNCS Series, pages 880-887, October 1998; (2) Fleute M, Lavallee S, Julliard R. Incorporating a statistically based shape model into a system for computer-assisted anterior cruciate ligament surgery. Medical Image Analysis. 1999 September; 3(3):209-22. However, other known methods of obtaining geometrical bone models in surgery exist (for example, matching medical image data such as CT, MRI, etc, to points acquired with a pointer or an ultrasound probe). Each of the above listed references is hereby incorporated by reference in its entirety.

In particular, the three dimensional shapes of the involved bones may be provided with image free techniques, such as using bone morphing software which is capable of extrapolating very few range data to obtain a complete surface representation of an anatomical structure (e.g., a bone). The specific details of bone morphing are set forth in the above references but in general, a complete surface model is built from sparse data using statistical shape models. In particular, the model is built from a population of a number of specimen (points), such as femur or tibia points, that are digitized. Data sets are registered together using an elastic registration method (e.g., the Szeliski and Lavallee method) based on octree-splines. Principal component analysis (PCA) is performed on a field of surface deformation vectors. Fitting this statistical model to a few points in performed by non-linear optimization. Results can thus be presented for both simulated and real data. This method is very flexible and can be applied to any structures for which the shape is stable.

In a preferred embodiment of the invention representations of the femur and tibial bones, or a portion thereof, are displayed on the screen. These models move on the screen in real time based on the motion of tracked femur and tibia. In a preferred embodiment of the invention the system guides the surgeon in manipulating the knee, by using the bone representations as visual aids. Knee manipulations are preferably preformed for both "normal" and "abnormal" joint motions. Normal motions can include passive flexion/extensions of the knee, with the tibia guided by the medial and lateral femoral condyles. Abnormal joint motions are those indicative of instability in the joint. In other words, the present system preferably is configured to collect data with the pointer 160 in order to perform bone morphing operations or procedures to thus obtain three-dimensional geometrical surface models of the bones. The kinematic data obtained from such motions could also be used to construct the BoneMorphing models, by for example, using the normal direction of a best fit plane to initialize the model. The knee manipulations may also be used to help plan the positions of the implants, for example, to obtain optimal soft tissue balancing around the knee. For example, a femoral component may be positioned such that the gap space between the tibial cut and femoral cut is equal when the knee is in flexion and in extension. Tensors can also be used to balance the knee, for example to apply equivalent forces on each condyle to distract the joint and create joint spaces. The planning of the position of the implants may also be a combination of soft tissue balancing criteria and bone surface, alignment and landmark criteria. Examples of such planning criteria are described in previously referenced United States Patent application No. 20050101966. It is preferable that the algorithm used to plan the position of the implants uses 3D surfaces models of the implants. The 3D surface models of the implants preferably include the outer implant surface and the inner implant surface where the inner implant surface, or at least a portion thereof, can correspond to the surface that needs to be cut out of the bone. This cutting surface can contain planar surfaces or more complex shapes such as curvilinear surfaces, spherical surfaces, or any shape of surface for that matter.

Once the desired position of the implant has been determined, the shape of the cutting surface on the bone can be determined, and the boundary between the cutting surface and the bone surface may be determined. Thus a perimeter around the desired cutting area can be defined and displayed on the computer screen 122.

The system 100 is particularly suited for joint replacement and resurfacing operations since the computer 120 can be configured for identifying and applying the anatomical coordinate system 170 to at least two bones 2, 4 of the joint. The anatomical coordinate system 170 can include directions, such as medial-lateral, proximal-distal, anterior-posterior, and so on. The system 100 thus can be configured for identifying landmark points on the surfaces of the bones 2, 4. Furthermore, the system 100 can be configured to measure the motion of one bone 2, 4 in space and to identify the centers of adjacent joints from the measured trajectories. The system 100 can measure the motion of one bone 2, 4 relative to another for various arcs of joint motion and degrees of joint rotation. In a further aspect, the present invention can provide a system for determining intra-operatively the three-dimensional shape of the bone surface in the vicinity of the articulating joint and in particular, in the vicinity of the joint surface area to be replaced. Preferably, the three dimensional shapes of the bones are provided with image free techniques.

Figure 3:
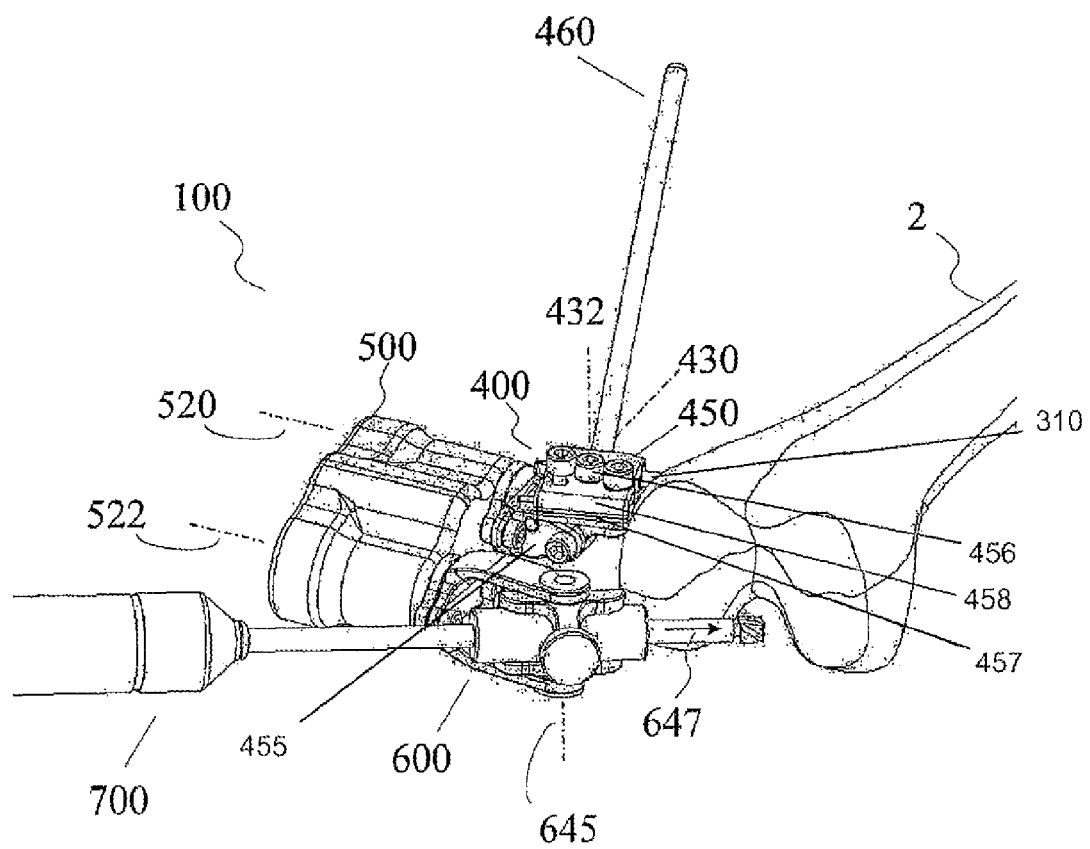
FIG. 3 is a robotic system for guiding joint replacement and resurfacing operations on at least a portion of a point of at least one bone.

The computer and robot assisted surgery system 100 according to one embodiment of the present invention is configured to provide a system for guiding joint reconstruction or resurfacing operations on at least a portion of a joint of at least one bone and includes a number of different components that cooperate with one another to perform the intended functions. As shown in FIG. 3, the system 100 can include fixation instrumentation (a fixation assembly) 300, an orienting apparatus 400, a positioning mechanism 500, and guiding instrumentation (guide assembly) 600 for guiding a tool 700, such as a cutting tool, e.g., a saw-blade or milling tool.

FIGS. 4a-7 illustrate one exemplary fixation assembly 300 which is intended to secure the orienting apparatus 400 and the positioning mechanism 500 onto the bone 2 (femur). As will be described in greater detail hereinafter, the orienting apparatus 400 and the positioning mechanism 500 are intended to align and position the guide assembly 600 with respect to the intended implant position in the femur 2. The guide assembly 600 is intended to provide an interface between the positioning mechanism 500 and the tool 700. As will be appreciated below, these system components are constructed to introduce a number of degrees of freedom into the system 100.

The fixation assembly 300 preferably includes a fixation means for rigidly fixing at least a part of the orienting apparatus 400 to the femur 2. For example, the fixation means can be in the form of a number of fixation fasteners that fix the orienting apparatus 400 to the femur 2. Suitable fixation fasteners include but are not limited to Stienman pins, threaded pins, screws, cannulated screws, fixation nails, or other types of fasteners. For ease of simplicity, these various means of fixation will be hereinafter generally referred to as fixation pins 310. The fixation pins 310 are elongated structures and each can include a head portion and typically includes a sharp, pointed distal end 312.

The fixation assembly also includes an anchor element 320 that is fully or partially inserted inside the femur 2. The illustrated anchor element 320 has an elongated body 322 that is at least part hollow and includes a first open end 324 and an opposing second closed end 326. The first open end 324 can include a first locking or locating feature 326, such as a notch, for forming a keyed type coupling with a guide element 330 described below. The illustrated anchor element 320 has a cylindrical body 322 and includes a number of through holes 328 passing therethrough, as well as a having a central bore 325 that is open at the first end 324. More specifically, the through holes 328 are formed through the side of the anchor element 320 between the first and second ends 324, 326. The number of and the size of the through holes 328 are selected so that the through holes 328 accept the fixation pins 310. In other words, the fixation pins 310 are slidingly received through the holes 328 in the body 322 so that they can pass completely therethrough into the femur 2. The anchor element 320 can be relatively short so as not to enter substantially into the intremedulary canal in the diaphyseal portion of the femur 2.

A cylindrical body 322 allows the surgeon to control the rotational position of the fixation pins 310 with respect to the bone 2 after the anchor 320 is inserted through the drill hole and into the bone 10. Alternatively, a non-circular cross-sectional shape could be incorporated into at least a portion of the anchor, to block rotations and increase stability. For example, a star shape could be used near the distal end of the anchor 320 so that rotation can be controlled, while the anchor 320 is partially inserted, and then fixed once it is fully inserted.

Alternatively, a longer anchor 320 that enters the intramedullary canal at least partially could be used to improve fixation stability if needed.

Figure 4A:
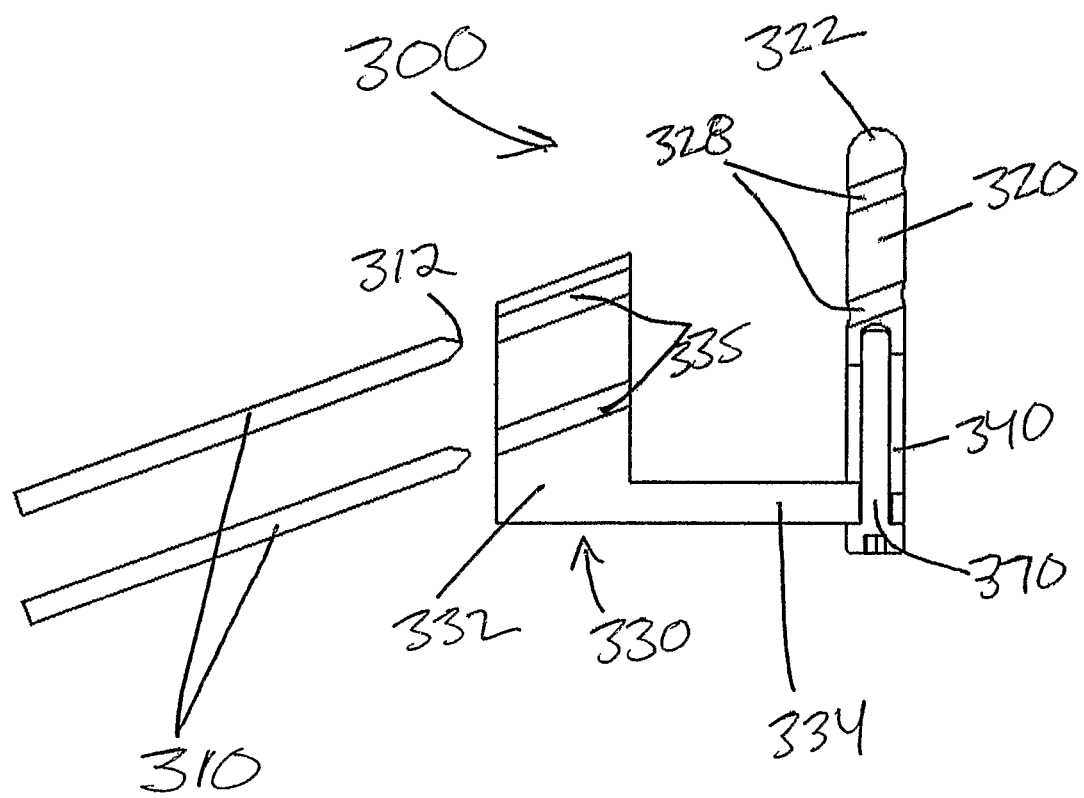
FIG. 4a is a side elevation view, in cross-section, of a fixation instrument for use with a guide system of the robotic surgery system of FIG. 3.
Figure 5:
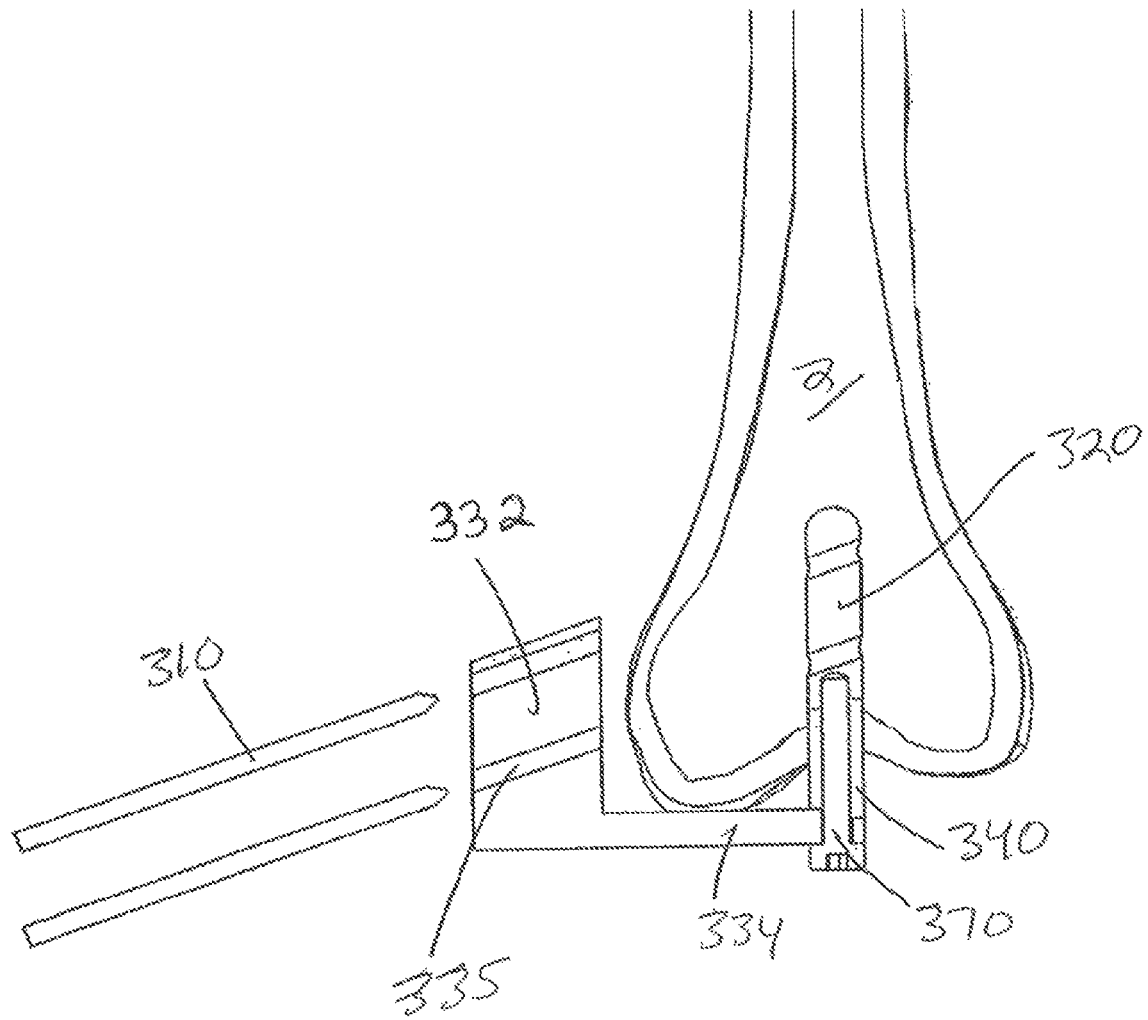
FIG. 5 is a side elevation view, in cross-section, of the fixation instrument of FIG. 4a inserted in a distal femur.
Figure 6:
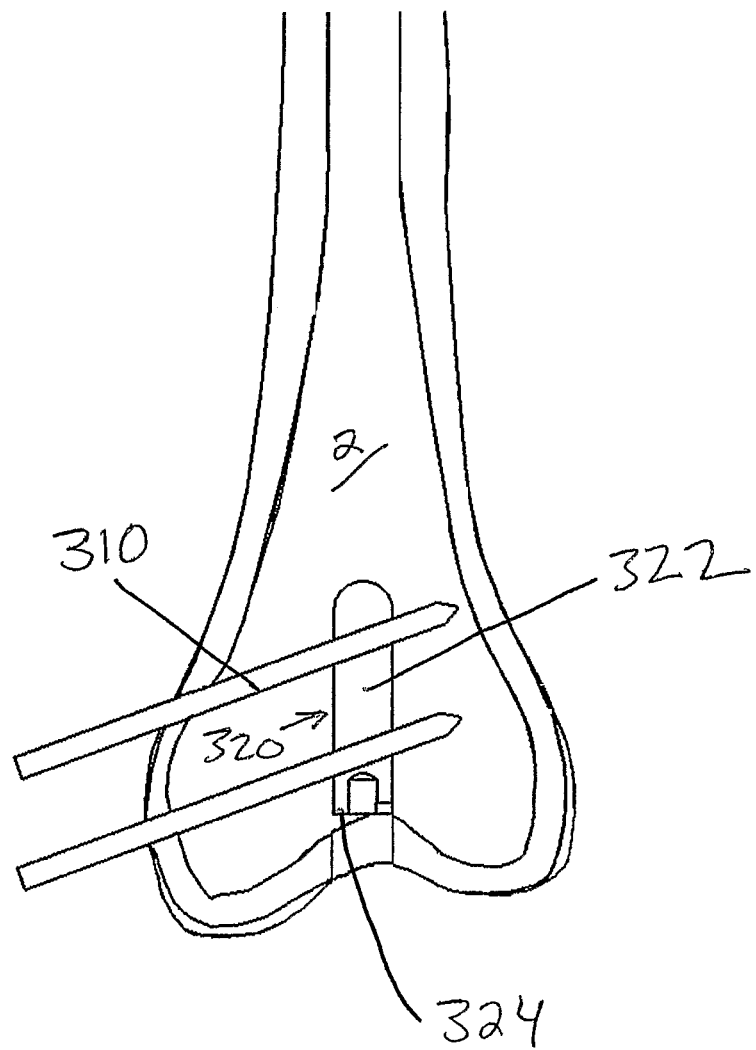
FIG. 6 is a side elevation view, in cross-section, of the fixation instrument inserted in the distal femur with a pin guide removed.

The guide element 330 is configured to be rigidly yet removably attached to the anchor element 320 and can be used to guide the insertion of objects so that it each engages one of the through holes 328 formed in the body 322 of the anchor element 320. For example, the guide element 330 can be used to guide the insertion of the fixation gins 310 or guide wires or the insertion of a bone drill or the like for making a hole in the femur 2, so that these objects engage and pass through the holes 328 formed in the body 322 to therefore be anchored to the bone 2. FIG. 4a illustrates the guide element 330 being removably coupled to the body 322 of the anchor element 320, while FIG. 5 shows these parts inserted into the distal femur. FIG. 6 shows the anchor element 322 inserted into the distal femur with the fixation pins 310 passing therethrough and the guide element 330 being removed.

Figure 7:
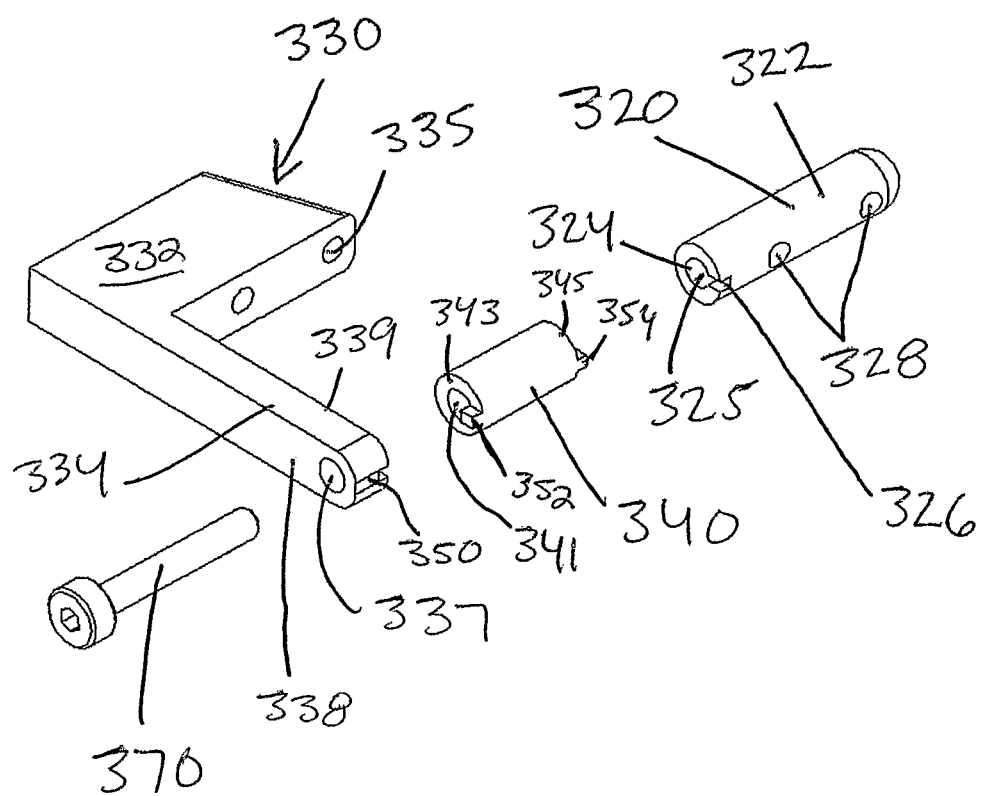

As best shown in the exploded view of FIG. 7, the guide element 330 includes a base portion or body 332 with an arm 334 extending outwardly therefrom. As best shown in FIG. 4a, when the guide element 330 is mated with the anchor element 320, the base portion 332 is disposed on an outside of the femur 2, while the arm 334 extends across ether below or above the bone, in this case below the distal portion of the femur 2, so as to position the arm 334 in proper relationship with the anchor element 320 to permit the anchor element 320 to be inserted into the distal femur 2.

Figure 4B:
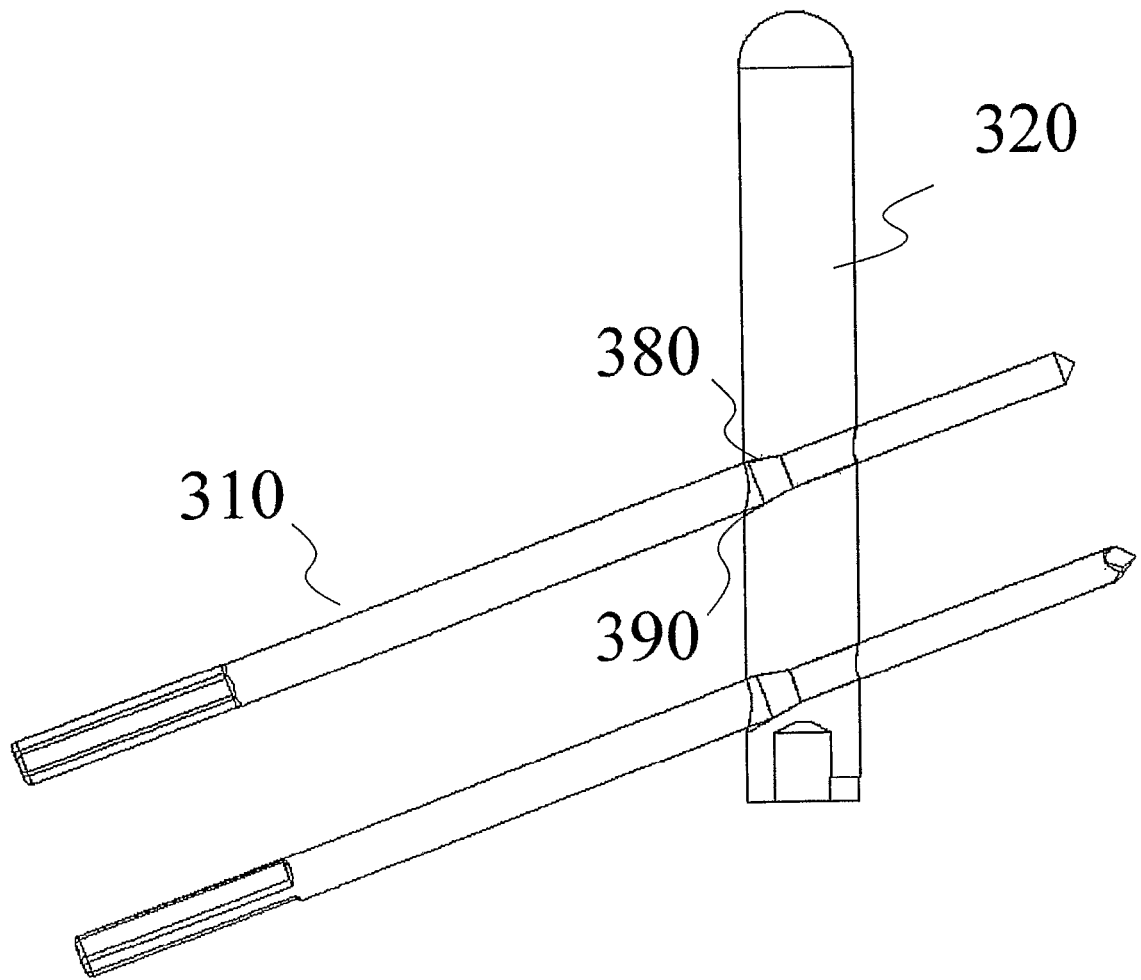

The base portion 332 contains a number of through holes 335 formed therein which receive the fixation pins 310 and more importantly, the holes 335 are substantially collinear with the holes 328 in the body 322 of the anchor element 320 so that when the fixation pins 310 are inserted and passed through the holes 335 of the guide element 330 they exit the body 322 and pass across a space between the two bodies 322, 332 where the femur 2 is present, through fixation holes formed in the femur 2 and then into the holes 328 of the anchor element 320 as shown in the figures. It will be appreciated that the holes 328, 335 are made substantially collinear by fixedly attaching the guide element 330 in a predetermined orientation relative to the anchor element 320. More specifically, when the guide element 330 is coupled to the anchor element 320, the proper alignment between the holes 328, 335 results. The holes 335 are thus substantially parallel to one another. At least a portion of the pins could be threaded. As illustrated in FIG. 4b, the pins 310 could also have a tapered portion 380 somewhere along their length. Thus the pin can have more than one diameter, and any portion can be threaded. The taper in the pins can interface with a corresponding taper in the holes of the anchor element 320, so that when the tapered portion of each pin comes into contact with the anchor, a force is produced that tends to push or pull the anchoring element against the bone for increased stability.

In yet another instance of the invention, anchor element 320 can be constructed to expand inside the bone, for example, when at least one fixation pin 310 is inserted. The expansion mechanism can be realized in a number of ways. For example, the anchor element 320 can have a thin slot (not shown) cut thought it (for example, about 1 mm thick), where the slot is coplanar to the axes of the pin holes 380, dividing each of them into two portions, an anterior and posterior portion. The slot can start from one end of the anchor element (for example the distal or proximal end) and can stop just before the opposite end, leaving some material at the opposite end to act as a hinge or flexure joint to facilitate the expansion action. The holes 328 in the anchor element can be configured with a diameter smaller than the largest diameter of the pin such that when pin 310 is inserted into hole 328, the larger pin diameter enters the smaller hole and tends to expand the effective diameter of the anchor element, elastically deforming the flexure joint and prying apart the two inner faces of the slot. In yet another variation of the invention, at least one of the holes can be absent, allowing the complete diameter of the pin to pry apart the anchor element when it enters the slot.

The arm 334 of the guide element 330 has a through opening or bore 337 formed at a distal end thereof such that the bore 337 passes through an underside 338 to a topside 339 of the arm 334. An axis of the bore 337 intersects axes of the holes 335 since the axis of bore 337 is not parallel to the axes of holes 335.

It will be understood that the guide piece 332 can include a sliding joint (not shown), such as a "dove tail" or "T" joint, located between the arm 334 and pin holes 335, with a direction parallel to pin holes 335. This allows the guide holes to be slid directly up against the bone surface to increase rigidity during drilling or pinning, while maintaining the co-linearity between the guide holes 335 and the anchor holes 328. In addition, the guide face that touches the bone surface can contain at least one sharp spike to prevent it from sliding on the bone surface during pinning or drilling.

In a preferred embodiment, the robot fixation pins 310 are installed in the femur before the femoral reference marker 142 is attached to the bone. The femoral reference marker 142 can then be attached directly to the robot fixation pins 310, via a base element 450 that fits and clamps onto the exposed portion of the robot fixation pins (FIG. 3). This minimizes the amount of screws placed in the bone. The femoral reference marker can be attached to the base element via an extending structure 460 having several centimeters in length, so as to ensure the reference marker is visible by the camera and does not interfere with the robot or other instruments during the procedure. The base element has a coupling interface to connect with the robot manual orientation system 400. In another embodiment, at least one of the manual orientation degrees of freedom 432 is incorporated directly into the base element. At any time during the procedure, the surgeon can check if the fixation pins or reference marker have moved relative to the bone by placing the point probe 160 on a confidence point such as an identifiable point on the bone surface or on anther small screw or pin (not shown) placed in the bone.

To couple the guide element 330 to the anchor element 320, a coupling spacer 340 is provided to mate with and be disposed between the arm 334 and the anchor element 320. The spacer 340 is a generally hollow member that has a through bore 341 formed therethrough from a first end 343 to a second end 345.

The arm 334 preferably includes a second locking or locating feature 350 that is complementary to and engages a third locking or locating feature 352 formed at the first end 343 of the spacer 340. The spacer 340 also includes at the second end 345 a fourth locking or locating feature 354. In the illustrated embodiment, both the third and fourth locating features 352, 354 are in the form of a tab or detent or protrusion formed at the respective end and extending outwardly beyond the respective ends of the spacer 340. The protrusions 352, 354 extend in opposite directions but along the same axis of the spacer 340. The protrusion 354 is complementary to the notch 326 so that it can be received therein to couple the second end 345 of the spacer 340 to the anchor element 320. Similarly, the protrusion 352 is complementary to the slot or opening 350 formed in the arm 334. It will be appreciated that when the protrusions 352, 354 engage the second locating feature 350 (e.g., a longitudinal slot or notch formed in the arm 334) and notch 326, respectively, each of the three parts (anchor 320, guide 330 and spacer 340) is prevented from rotating independent of the other parts. These locating features thus not only locate each part relative to the other part but they also rotationally lock each part with respect to the other parts.

As best shown in FIG. 7, the guide element 330, spacer 340 and anchor 320 are coupled to one another by means of a fastener 370, such as a pin. The pin passes through the bore 337 formed in the arm 334, then passes through the bore 341 of the spacer 340 and into the bore 325 of the anchor element 320. Advantageously, the guide element 330, as well as the spacer 340, can be made to disassemble from the anchor element 320 so that is can be removed and not interfere with the cut after the fixation pins 310 have been properly inserted into the femur 2. The entire anchor fixation system defined by the above parts has the advantage of increased rigidity in particularly soft or weak bone, which is often present in patients suffering from osteoarthritis. However, in patients with very hard and strong bones, using fixation pins 310 or screws alone can be enough to obtain a sufficiently rigid connection.

Once the fixation pins 310 have been properly located in the femur 2 to support the other components of the overall system 100, the orienting apparatus 400 is then attached to the fixation pins 310. FIG. 3 illustrates one exemplary orienting apparatus 400 according to the present invention. The orientating apparatus 400 is generally formed of two parts, namely a base 450 and a second part that is movably coupled to the base 450 and provides an interface to the positioning mechanism 500 (FIG. 3). The base 450 has a body that attaches to the fixation pins 310 by a number of different means, including providing a clamping mechanism. Such a claming mechanism can be realized using a slot cut out of the body, where at least a portion of the slot intersects with the two axes of the fixation pins 310. A clamping screw, can be arranged in-between in-between the two pins such that when the screw is tightened, the body flexes and clamps onto the fixation pins 310. Slot can be made by wire cutting, for example, and the slot path cut can be made so as to have two areas of flexure in the body such that the clamping action is a parallel one, applying a more or less equally on force on each fixation pin.

Figure 8:
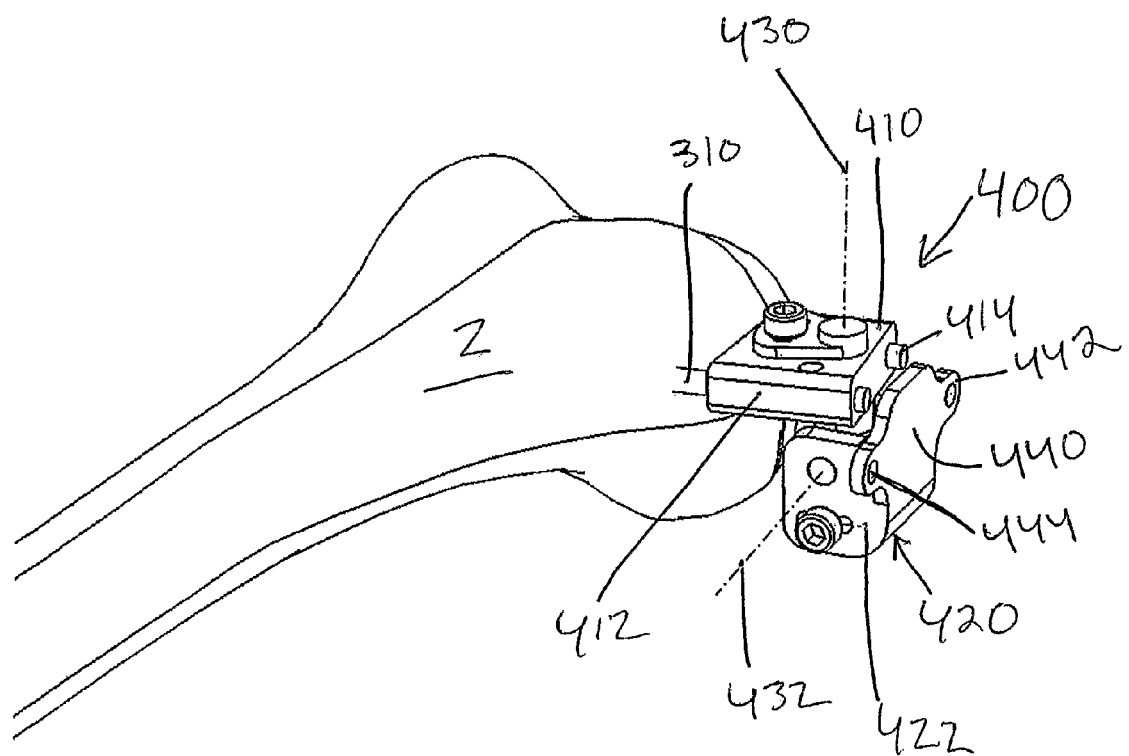
FIG. 8 is a perspective view of an orienting apparatus of the guide system of the computer assisted surgery system of FIG. 3 fixed to a side of the distal femur.
Figure 9:
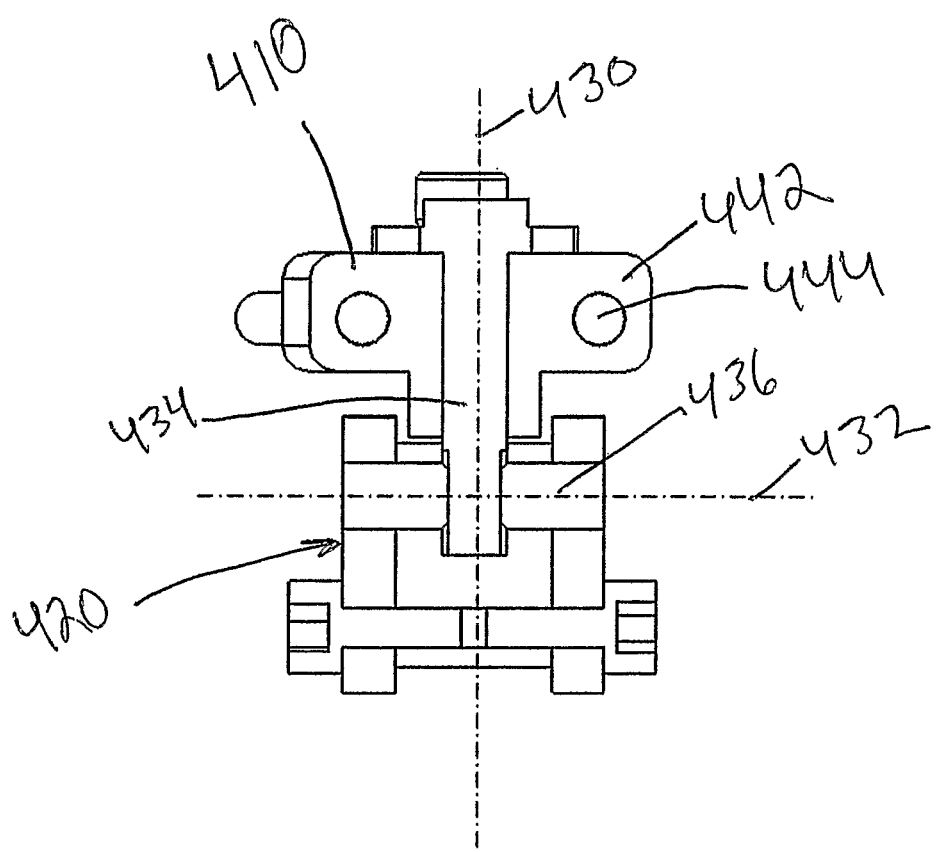
FIG. 9 is a cross-sectional view of the orienting apparatus of FIG. 8.

FIGS. 8 and 9 illustrate another exemplary orienting apparatus 400 according to the present invention. Again, the orientating apparatus 400 is generally formed of two parts, namely a base 410 and a second part 420 that is movably coupled to the base 410 and provides an interface to the positioning mechanism 500. The base 410 has a body or sliding joint 412 that attaches to the fixation pins 310 by a number of different means, including providing complementary fastening members, such as threaded screws 414, associated with the body 412. These screws 414 can be used to rigidly fix the base 410 of the orienting apparatus 400 onto the pins 310. The fixation pins 310 are aligned with the screws 414, which are then tightened to cause the body 412 to be securely and fixedly attached to the fixation pins 310. As illustrated, the screws 414 run along a length of the base 410.

The sliding joint described above provides a means of easily separating the fixation assembly 300 from the base 410 or 450.

In another embodiment, the base 410 or 450 of the orienting apparatus 400 is integral to the fixation assembly 300 and more particularly, to the pin guide 330 and fixation pins 310 such that once the fixation pins 310 are inserted, the base 410 is already fixed upon the femur 2. This will save considerable time and effort during the fixation step of the procedure since the step of fixedly attaching the orienting apparatus 400 to the fixation pins 310 is eliminated.

The second part 420 is movably attached (e.g. pivotally) to the base 410 so as to provide the orienting apparatus 400 with at least one rotational degree of freedom. This rotational degree of freedom rotates in a direction that is generally aligned with the varas/vargus direction of the implant. As is known in the field, the term "varus" refers to an inward direction and the term "valgus" refers to an outward direction and these terms refer to the direction that the distal part of the joint (or bone depending upon the point of reference) points. This degree of freedom can be lockable by means of a fastener, such as a screw, or by means of a quick locking cam mechanism.

Preferably, the orienting apparatus 400 includes another rotational degree of freedom. As illustrated in FIGS. 3, 8, and 9, the orienting apparatus 400 can include a first rotational degree of freedom along axis 430 and a second rotational degree of freedom along axis 432, with one of these rotational degrees of freedom being in the varas/vargus direction and the other being generally aligned with the transverse rotation directions of the implant. This additional rotational degree of freedom can likewise be lockable by means of a fastener (screw) or by means of a quick locking cam mechanism.

As best shown in the cross-sectional view of FIG. 9, the rotatable second part 420 is connected to the base 410 at least along the axis 430 as by means of a first shaft or the like 434 to thereby permit the second part 420 to rotate about the axis 430. The second part 420 includes a body 422 that is rotatably coupled to the first part 434 to permit rotation of the body 422 about the first axis 430. The body 422 of the second part 420 is also preferably rotatably coupled to a second part 436 to permit rotation of the second part 420 about the second axis 432.

Figure 10:
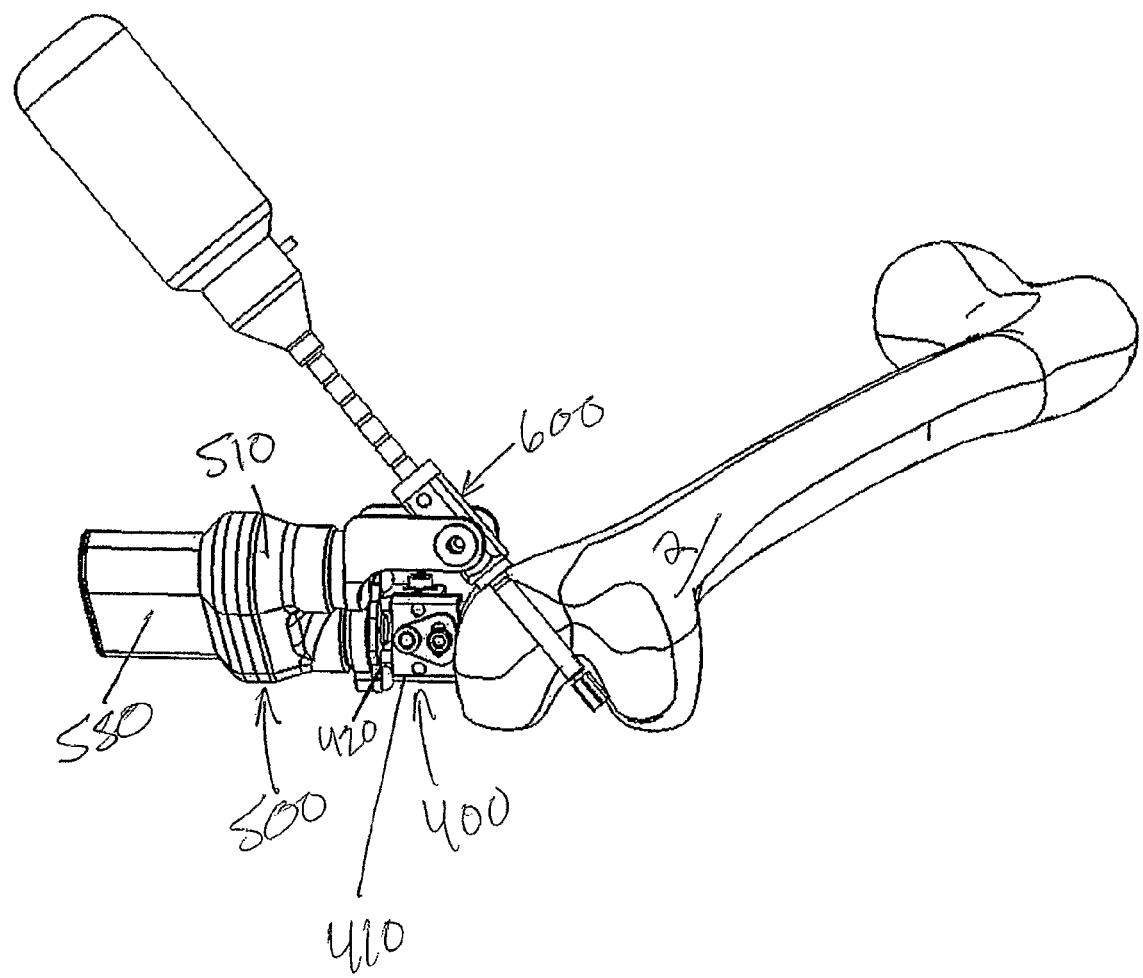
FIG. 10 is a perspective view of a positioning mechanism attached to the orienting apparatus with a milling system attached thereto for performing resurfacing operations on the bone.

Thus, the body 422 has at least two degrees of rotational freedom with respect to the base 410. In this manner, the orienting apparatus 400 (adjustment system) is similar to a universal joint, with two rotational axes arranged perpendicular and intersecting to one another as illustrated in FIGS. 8-9. These two rotational axis can also be non-intersecting as shown in FIG. 3. Here, the varus/valgus rotation axis 432 is along the axis of screw 456, and the internal/external rotation axis 430 is about pin 452. The body 422 of the second part 420 includes a mounting or interface section generally indicated at 440. This section 440 can be in the general form of a mounting plate which is preferably planar in nature as illustrated. As described below, the positioning mechanism 500 is coupled to the orienting apparatus 400 by being mounted to the section 440. The section 440 is formed along one face of the body 422 that faces away from the base 410. In the illustrated embodiment, the section 440 has a pair of spaced, outwardly extending wings or tongues 442 that have openings 444 formed therethrough to receive fasteners or the like to fixedly couple the positioning mechanism 500 to the orienting apparatus 400. In another embodiment, especially when only the fixation pins 310 are used alone, the orienting apparatus 400 can be fixed as indicated in FIGS. 3 and 10, such that rotational axis 432 corresponds to the "varus" rotation.

In one embodiment and as will be appreciated more below, the fixation assembly 300 and the orienting apparatus 400 provide a fixation and adjustment system that secures the robotic components of the present invention to the femur 2 and incorporates a two degree of freedom adjustment mechanism which permits the surgeon to align (e.g., manually) an axis associated with the robotic component to the implant profile in both the frontal and transverse (or axial) planes 50, 60 (FIG. 1).

The positioning mechanism 500 is connected to the orienting apparatus 400 and similar to the orienting apparatus, the positioning mechanism 500 is constructed so that it has a rotational degree of freedom. More specifically, the positioning mechanism 500 is constructed so that it includes at least two rotational degrees of freedom that have rotational axes arranged substantially parallel to one another, and substantially orthogonal to the axes 430, 432 of rotation of the orienting apparatus 400. Thus, the rotational axes of the positioning mechanism are substantially parallel to the flexion/extension axis of the implant.

As shown in FIGS. 10-18, the positioning mechanism 500 includes a body 510 that has a first section 512 and a second section 514 spaced therefrom. Each of the first and second sections 512, 514 includes an arm or finger 516, 518, respectively, at distal ends thereof and includes head portions 517, 519 at opposite ends thereof for mating with an actuator as described below. The first section 512 includes a first rotational axis 520 (FIG. 3) of the positioning mechanism 500, while the second section 514 includes a second rotational axis 522 (FIG. 3) of the positioning mechanism 500 which is substantially parallel to the first rotational axis 520. In the illustrated embodiment, the first section 512 and therefore, the first rotational axis 520, is coupled to the orienting apparatus 400, while the second rotational axis 522 is attached to the guide assembly 600, which provides an interface between the positioning mechanism 500 and the tool 700. As previously mentioned, the orienting apparatus 400 and the positioning mechanism 500 are intended to align and position the guide assembly 600 with respect to the intended implant position in the femur 2.

A central section 515 separates the first and second sections 512, 514, such that the first and second rotational axes 520, 522 of the positioning assembly 500 are separated by a distance such that the combined rotation of the first and second rotational axes 520, 522 changes the guide assembly 600 positioning in the sagittal plane 70 (FIG. 1) in one rotational degree of freedom, as well as two translational degrees of freedom. These degrees of freedom correspond substantially to flexion/extension implant rotation, AP implant positioning, and PD implant positioning.

Within each of the first and second sections 512, 514, there is a rotatable element, such as a shaft, that rotates about one of the first and second rotational axes 520, 522, respectively. In other words, the first section 512 has a first rotatable element associated therewith, while the second section 514 has a second rotatable element associated therewith. Each of the first and second rotatable elements is operatively coupled to an actuator or the like that selectively imparts controlled rotation to one of the first and second rotatable elements. At the distal ends of the first and second sections 512, 514, the first and second rotatable elements can be operatively coupled to another member, such as the orientating apparatus 400 or the guide assembly 600, to translate rotation to the members or to rotate the positioning mechanism 500 relative to the member, keeping the cutting guide axis substantially aligned with the axes 522, 520.

The two rotational axes 520, 522 of the positioning mechanism 500 can be actuated manually or the axes 520, 522 can be actuated in an automated manner. The actuation can be caused by any number of different types of mechanisms, including any type of actuation motor, including electromagnetic, piezoelectric, brushless, stepper, pneumatic, etc., or the actuation can be caused by any other known means of actuation. For ease of illustration, the actuation of the rotatable elements is discussed as being caused by an actuator, such as a motor, which is generally indicated at 550 and is associated with one of the rotation axes 520, 522 of the positioning mechanism 500. Thus, the positioning mechanism 500 can be discussed as having a pair of actuators 550 for the two rotatable elements in the two sections 512, 514. The actuators 550 can be in the form of a single module (FIG. 14) or motor pack that is operatively coupled, in a detachable manner, to the heads 517, 519 of the positioning mechanism 500 such that each of the first and second rotatable elements in the two sections 512, 514 is operatively coupled to one of the actuators 550 (motor or the like). The actuators can thus be in the form of a pack that contains two independently operated motors and is configured to detachably interlock with the two heads 517, 519 of the positioning mechanism 500. The body 510 of the positioning mechanism 500 can be thought of as a gear and brake unit that is detachably coupled to the actuator (motor) unit 550.

In another different embodiment, the motors are directly integrated into the gear unit such that they are in the same housing, as illustrated in FIG. 3. In particular, the motors can be arranged within the housing 500 so that they lie in between 524 the two axes of rotation 520 522, and are connected to the axes via gears, for example, spur gears (not shown). This makes for a particularly compact unit.

In the automated embodiment, where the two rotatable elements are actuated automatically, the surgeon does not have to align manually by hand both the flexion/extension implant rotation and the AP and PD implant positioning. This results in a savings of time during the position step of the procedure and makes the overall system 100 easy to use for the surgeon. Furthermore, precision gears can be included at each rotational axis 520, 522 (e.g., at each rotatable element) of the positioning mechanism 500 to increase the guide positioning accuracy. It will therefore be appreciated that upon actuation, one of the rotatable elements is rotated about its respective rotational axis to directly translate a rotational force to the member that is operatively coupled thereto. In the case when the first rotatable element is coupled to the orienting apparatus 400, the orienting apparatus 400 can be caused to rotate about the first rotational axis 520, while when the second rotatable element is attached to the guide assembly 600, the guide assembly 600 and the tool 700 attached thereto can be caused to rotate about the second rotational axis 522.

The positioning mechanism 500 can also include a brake mechanism 560 as shown in FIG. 10. The brake mechanism 560 is constructed to prevent the first and second rotatable elements from rotating about rotation axes 520, 522 as long as the brake is not released. The brake mechanism 560 can be electromechanical or manual and can be spring loaded such that the surgeon must interact with an interface, such as for example, the pressing of a button 562 or turning of a knob to disengage the brake mechanism 560. In addition, the brake mechanism 560 can be configured so that a single interface button disengages the brake mechanisms from both rotation axes 520, 522 simultaneously. The brake mechanism 560 can be configured to block rotation at the transmission level of the precision gear reducer inputs so that any small rotational deviations caused by the engaging action of the brake are reduced by the gear reduction ratio at the guide positioning level.

According to one exemplary embodiment, the brake mechanism 560 is in the form of a manual spring-loaded brake that is disposed in between the zero-backlash gear inputs and the motor outputs. In this embodiment, the surgeon must hold the safety button 562 in order to release the brake and free both gear inputs to rotate.

Using brake mechanism 560 has several advantages for safety and convenience. When using actuators (e.g., motors) to position the guide assembly 600 (e.g., cutting guide), the brake mechanism 560 ensures that (1) the guide assembly 600 maintains its position regardless of the state of the actuators; and (2) the actuators cannot move the guide assembly 600 unexpectedly if the button 552 is not depressed. Additionally, since the actuators 550 can be removably attached to the gear unit of the positioning mechanism 500, they can be easily replaced during the procedure in case of failure or malfunction. A system that is configured with brake mechanism 560 and removable actuators 550 also has the advantage that the overall weight of the positioning mechanism 550 can be reduced during the cutting stage. Because of the quick-release brake mechanism 560, the surgeon only needs to mount the motors 550 to the gear interface that can be present in the heads 517, 519 of the positioning mechanism 500 before making each of the five femoral TKA cuts to align the guide assembly 600 to the cutting plane.

Since the brake mechanism 560 bears the loads applied to the guide assembly 600 during the cutting phase, the motors 550 need only provide enough power to position the cutting guide assembly 600. The motors 550 can be lower torque motors 550 that provide sufficient torque to lift the cutting guide 600 with the brake released, but not enough force to pose any significant threat. Moreover, the surgeon can overpower the motors 550 and backdrive the system in the case of a controller malfunction. In case of a motor or cable failure in surgery, the actuators 550 are designed as a modular system in which the motors 550 are encapsulated in a separate housing so that they can easily be detached from the gear unit in the positioning mechanism 500 and replaced. Therefore, this configuration allows a hospital to use the motors 550 until the end of their lifespan and then to dispose and replace the motors 550 after failure without having to stop the surgery and dismount the robotic parts. Finally, because of the quick-release brake mechanism 560, the surgeon only needs to mount the motors 550 to the gear block interface in the positioning mechanism 500 before making each cut to align the guide assembly 600 to the cutting plane, the motor unit and power cable do not need to be connected to the robot during a cutting phase or milling phase when the surgeon is typically standing directly beside the knee. This permits the guide 600 to be very compact and lightweight. This option becomes more important in patients having very poor quality bone where the fixation rigidity could be compromised.

Figure 11:
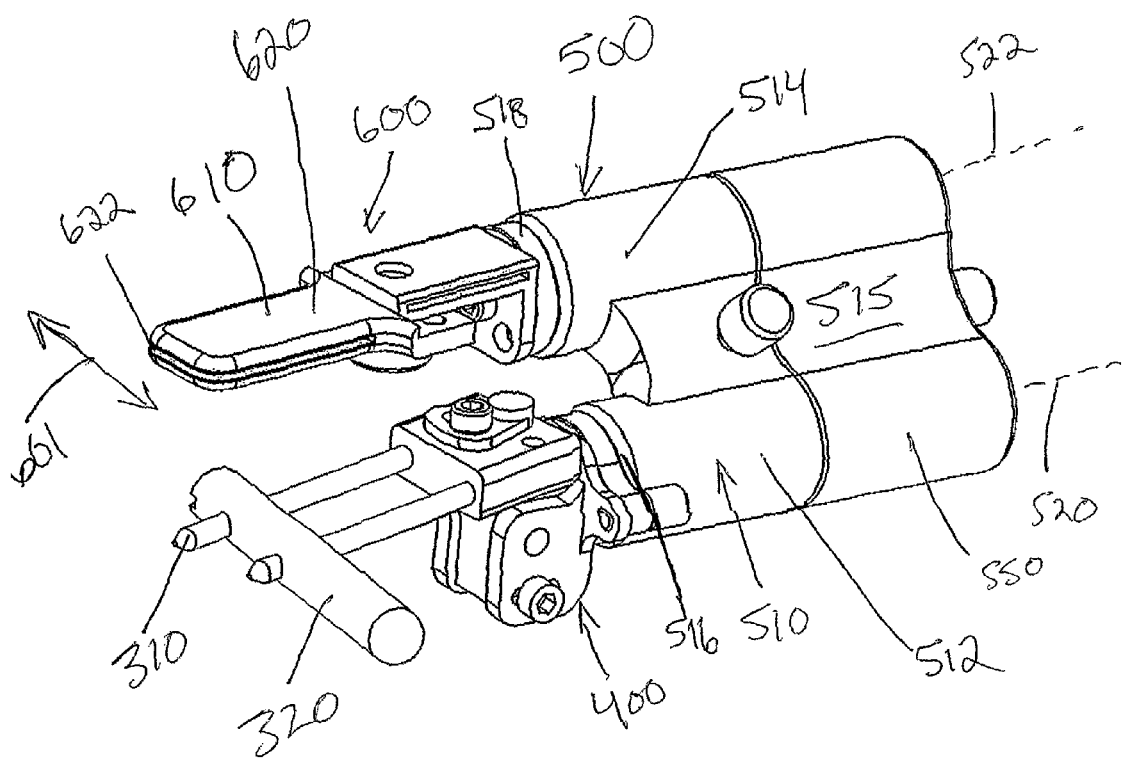
FIG. 11 is a perspective view of the positioning mechanism of FIG. 10 attached to the orienting apparatus with a sawing guide attached thereto.

One exemplary guide assembly 600 is shown in FIG. 11 and the modular nature of the system 100 of the present invention permits attachment to the various cutting guide interfaces 600, such as saw-guides or milling tool guides. FIG. 11 shows an exemplary saw-blade guide 610 being attached to one of the first rotatable element associated with the first section 512 of the positioning mechanism 500. The illustrated saw-blade guide 610 preferably includes a slot for receiving a saw-blade. The saw-blade guide 610 can include a linear sliding joint in the plane of the cut so that the saw-blade tip can always be slid up to the start of the cut. This permits the saw-blade guide 610 to slide linearly in the direction indicated by the arrow 601.

The illustrated saw-blade guide 610 includes a guide arm 620 that extends outwardly from the positioning mechanism 500 and is operatively coupled to the first arm (distal end) 516 of the first section 512 such that rotation of the first rotating element about the first rotation axis 520 results in rotation of the attached saw-blade guide 610 and guide arm 620 about the first axis of rotation 520. In this way, the guide assembly 600 can be rotated to a desired location during the procedure so as to position the tool 700 which in the case of a saw-blade guide 610 is a saw-blade 700. By providing slot 622 and the linear movement along the arrow 601, this has the advantage to position the saw-guide directly up against the femur 2, minimizing the unsupported distance of the blade between the edge of the saw-guide slot 622 and the femur 2. This can minimize the cutting errors due to saw blade bending and skiving.

In order to position the saw-blade guide 610 as close as possible to the inner edge of each cut, a specific cutting order can be used. In particular, if the distal cut is made first, then making an anterior chamfer cut before making the anterior cut results in the saw-blade guide 610 being positioned at the start of both the anterior chamfer cut and the anterior cut. Similarly, making the posterior chamber cut before the posterior cut results in the saw-blade guide 610 being positioned at the start of both the posterior chamfer cut and the posterior cut.

Figure 12:
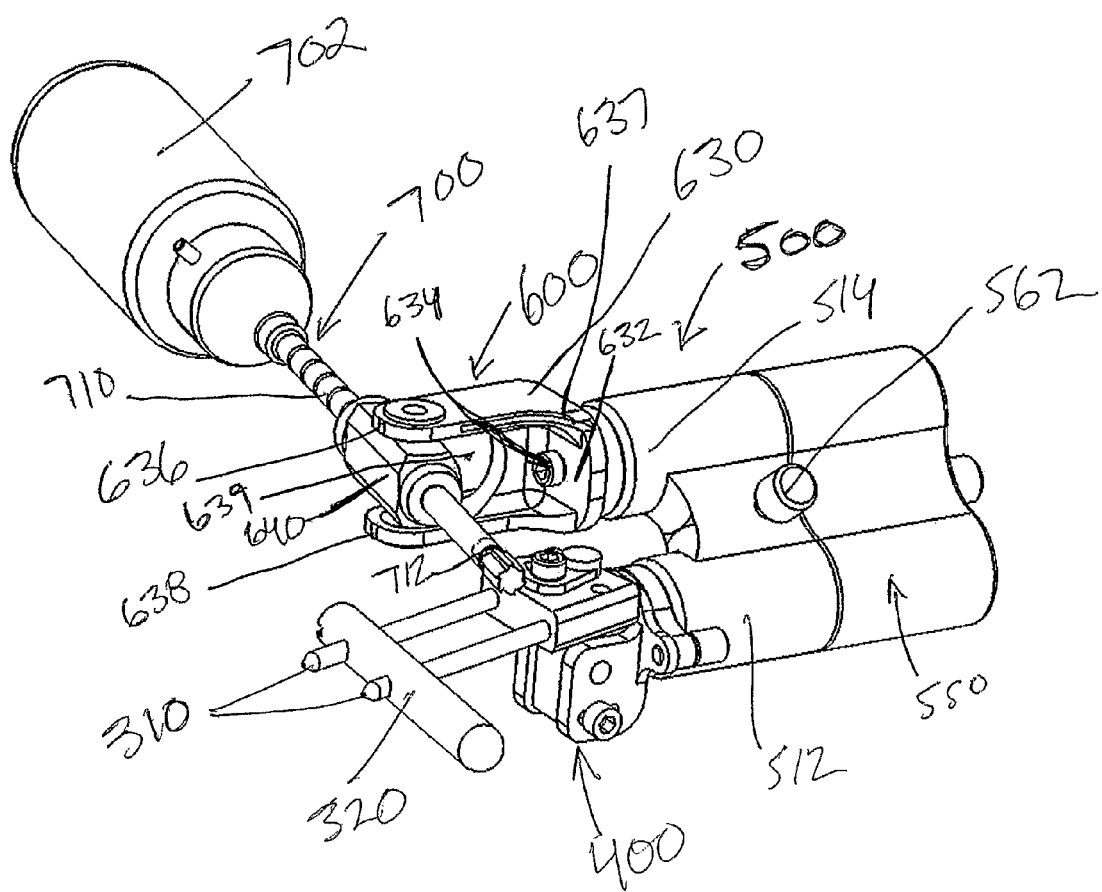
FIG. 12 is a perspective view of the positioning mechanism of FIG. 10 with the orienting apparatus and a milling system attached thereto, as well as the fixation instrument.
Figure 13:
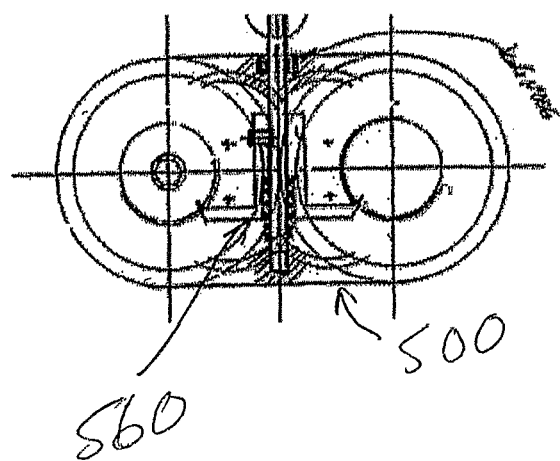
FIG. 13 is a cross-sectional view of one exemplary brake mechanism for the positioning mechanism.
Figure 14:
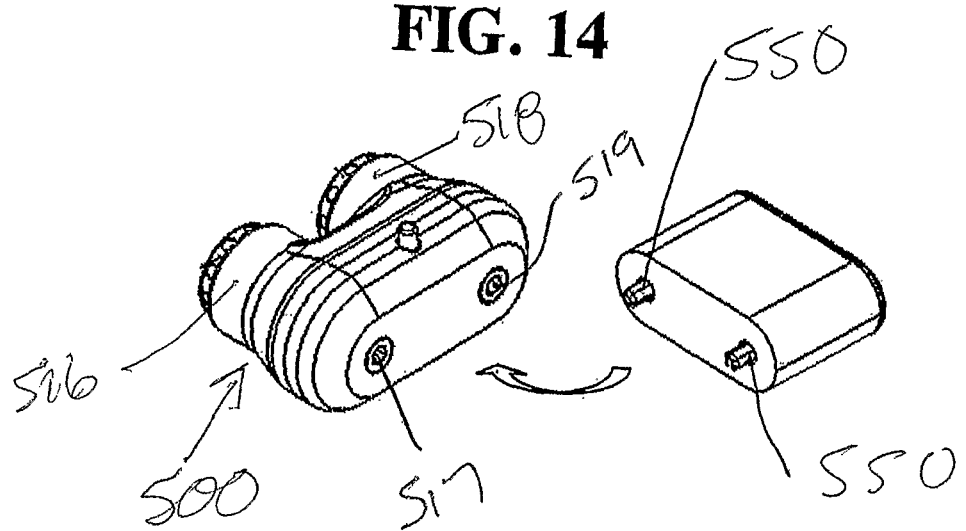
FIG. 14 is a perspective view showing the modular nature of the positioning mechanism.

FIGS. 12-13 illustrate the guide assembly 600 in the form of a milling guide 630 that is configured to be attached to the positioning mechanism 500 to guide a milling tool 700 instead of the saw-blade guide 610. As shown in FIG. 12, the milling guide 630 is rotatably coupled to the first rotatable element of the second section 514 of the positioning mechanism 500. The illustrated milling guide 630 includes a base portion 632 that can include a boss or shaft 634 that is operatively attached to the first rotatable element so that rotation of this element causes the base portion 632 and the remaining part of the milling guide 630 to rotate. A pair of guide arms 636 are provided and are integrally attached at first ends 637 to the base portion 632. The guide arms 636 are spaced apart from one another so that a space 639 is provided between the two guide arms 636, with the boss 634 being disposed between the two guide arms 636.

The distal second ends 638 of the guide arms 636 are open ends and preferably a milling tool joint 640 is disposed between the two second ends 638 of the arms 636. The milling tool joint 640 has a body 641 with one face 642 that is rotatably coupled to one arm 636, while the other face 646 of the tool guide block 640 is rotatably coupled to the other arm 636. The body 641 is thus capable of rotating about an axis within the space 639 formed between the two guide arms 636, as illustrated by the arrow 645 (FIG. 3), to thereby permit the tool 700 itself to be rotated relative to the milling guide 620, which itself can be rotated about the first rotation axis 520. In other words, the milling tool guide 620 for making planar cuts, such as those performed in TKA, can include at least one rotational degree of freedom (indicated by arrow 645 in FIG. 3) and at least one translational degree of freedom in the cutting plane, indicated by arrow 647 (FIG. 3). Thus, the joint 640 includes both elements of rotation and translation and therefore, can be thought of as having a rotational degree of freedom and a translational degree of freedom. The translational degree of freedom joint axis can be parallel to the axis of rotation of the milling tool 700. The axis of the milling tool 700 can intersect at right angles the rotational degree of freedom axis so as to avoid causing a moment about the rotational axis when sliding the milling tool in the translational direction, indicated by arrow 647 (FIG. 3). The rotational joint can be connected to the milling guide 620 and the translational joint can be connected to the rotational joint so as to realize a very compact form with a large range of motion.

At least one of the two degrees of freedom of the milling guide 620 can be lockable. Preferably, the degree of freedom that is lockable is the translational degree of freedom. This allows the surgeon to make the cut in sweeping motions using one degree of freedom at a time. These sweeping motions give better and more stable control of the milling tool 700 while making the cut.

Figure 15:
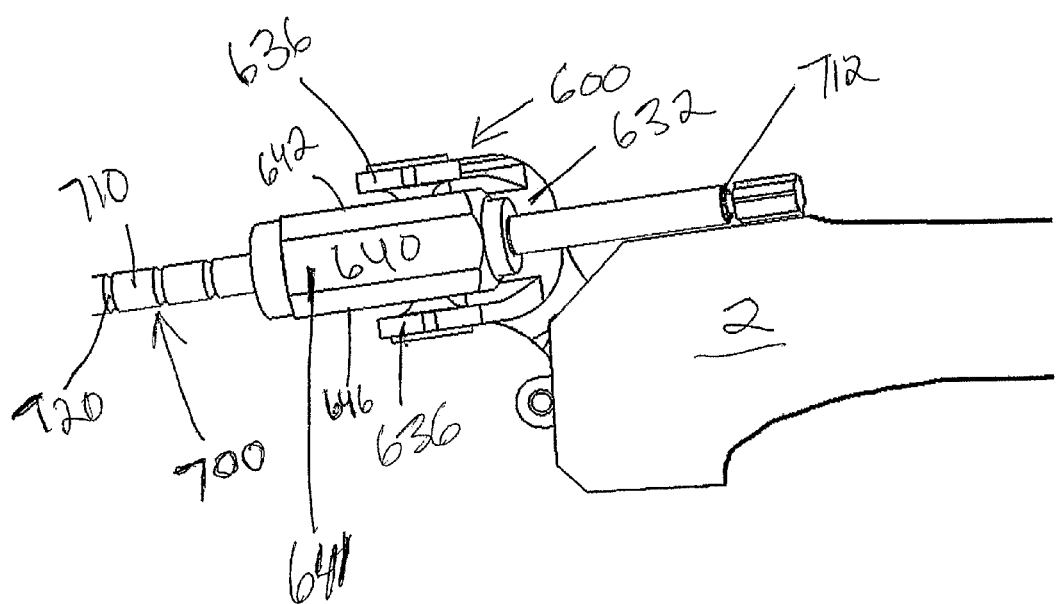
FIG. 15 is a side perspective view of the milling system milling the anterior cut plane with a straight side cutter.
Figure 19:
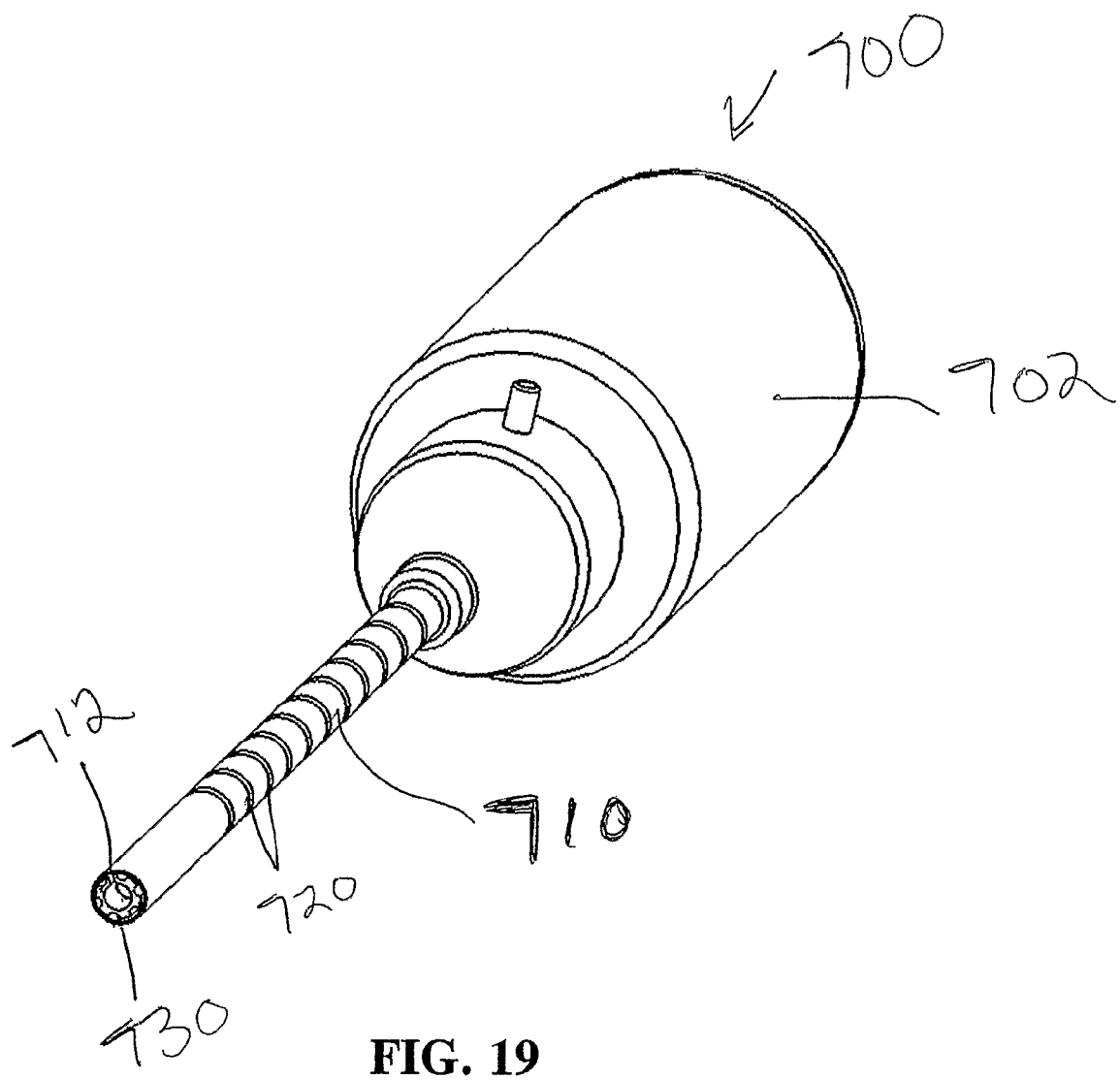
FIG. 19 is a perspective view of a milling tool of the milling system.

The interface between the milling tool attachment piece 710 and the translational joint 640 can be indexed so as to allow the milling tool 700 to be advanced in discrete intervals. As shown in FIGS. 12, 15 and 19, the milling tool 700 includes a base or body 702, with the tool attachment piece 710 being in the form of an elongated shaft having a distal tip 712 and extending outwardly from the body 702. The attachment piece 710 or shaft includes a number of indexing features 720 formed at spaced intervals along a length thereof. For example, the indexing features 720 can be in the form of circumferential notches formed in the attachment piece 710 and spaced apart from one another a predetermined distance. The distance between two consecutive notches 720 can be the same or the distance can be different. Preferably, these intervals are substantially equal to or slightly less than the axial length of the cutting tool 700. This maximizes cutting efficiency for a given milling cutter and minimizes the number of passes used to make the cut. Preferably, the indexing system is configured so that it can be switched on or off to accommodate surgeon preference or to allow simultaneous two degrees of freedom motion for following complex trajectories, for example, along the perimeter of a cut plane. In one embodiment, each notch 720 is numbered to provide data indicative of how deep the milling tool 700 is in the patient.

It will also be appreciated that both the cutting device and the milling device 700 has at least three markers so that the device is trackable by the position measuring device 110 using the coordinate system 170. In particular, the milling device 700 has an axis that has a known spatial relationship relative to the markers. Based upon the known spatial relationship between the drill or milling tip and markers, the position of the drill or milling tip is determined.

Preferably, the milling tool guide 620 can include a slot for guiding a saw-blade, permitting the milling tool 700 to be used for some cuts and the saw-blade to be used for the other cuts. This is particularly useful for making the posterior cut which is surrounded by soft tissues. The use of a continuously rotating cutting tool, such as the milling tool 700, may in some applications be associated with a higher potential risk than with an oscillating saw-blade. The above slot can also be used to attach a rigid body, for example, the planar probe 160 of the system 100.

Figure 20:
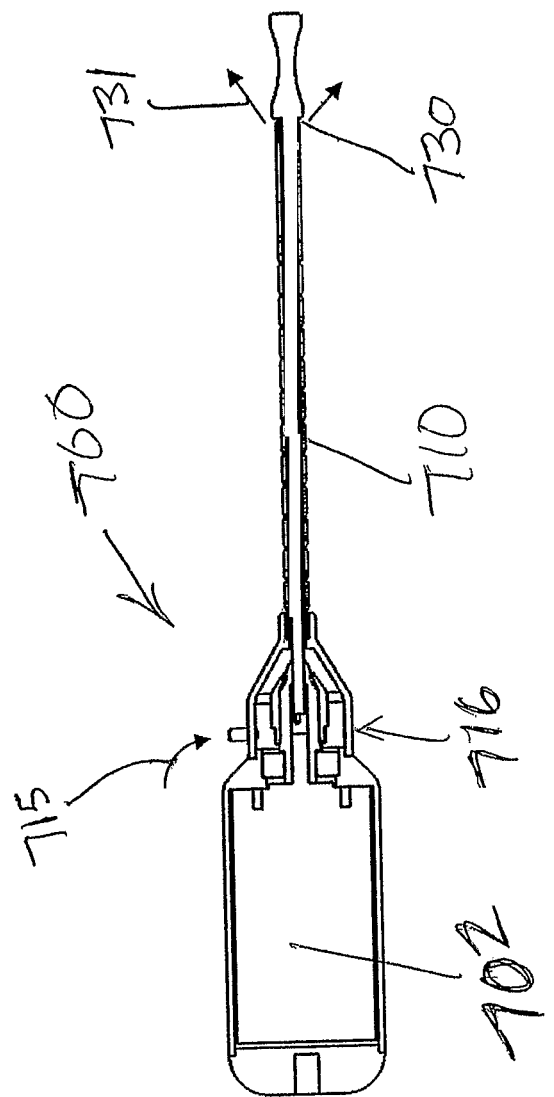
FIG. 20 is a cross-sectional view of the milling tool of FIG. 19 illustrating a milling irrigation system.

FIGS. 19-20 show the milling tool 700 in greater detail. The distal tip 712 of the milling attachment piece 710 contains a fluted bearing 730 for supporting the rotating cutter and for allowing fluid to pass through to irrigate the cutting side. The bearing 730 can be made out of low friction plastic materials and can also be disposable. The use of irrigation fluid helps to reduce the friction. FIG. 20 illustrates a milling irrigation system. Fluid enters through the base 716 of the attachment piece 710, as indicated by arrow 715, and travels within an interior bore of the attachment piece 710 before exiting through the fluted bearing 730, as indicated by arrow 731, to irrigate the cutting site in the vicinity of the cutting tool 700. A low profile ball or needle bearing that allows the fluid to pass in between the balls or needles can also be used.

Now referring to FIGS. 16-19 and according to another embodiment, the milling system of the present invention can be configured so as to allow the machining of non-planar cut surfaces. In this configuration, the longitudinal axis of the milling tool 700 is arranged so that it is parallel to the two rotational axes 520, 522 of the positioning mechanism 500 and the translational degree of freedom is used so as to drive the milling tool 700 along its axis. Here the positioning (motorized) mechanism degrees of freedom can be used to guide the motion of the milling tool 700 along the direction of the cut. The milling tool can be advanced along the cut by for example holding down the control system footswitch. The robot thus only moves the cutting tool whilst the footswitch is pressed and held down. Different footswitches can be used to control movement in different directions along the cut path. Alternatively, a force sensor can be incorporated into the robot and the movement can be controlled as a function of the forces applied by the surgeon. Thus the surgeon can directly control the position of the milling tool and feel the forces on the robot during cutting. Such control systems exist and are known, such as that used by the ACROBOT robotic system. Such systems are described in many publications, including Cobb J, Henckel J, Gomes P, et al, Hands-on robotic unicompartmental knee replacement, Journal of Bone and Joint Surgery—British Volume, 2006, Vol: 88, Pages: 188-197, ISSN: 0301-620X, and Jakopec M, Harris S J, Rodriguez y Baena F, et al, The first clinical application of a 'Hands-On' robotic knee surgery system, Computer Aided Surgery, 2001, Vol: 6, Pages: 329-339, ISSN: 1092-9088, which are hereby referenced in their entirety. Advancement of the milling guide 620 translational degree of freedom allows for the machining of different contours in three dimensions, one plane at a time.

In one embodiment, the translational degree of freedom is also motorized and sculpting of the bone can be accomplished in all three dimensions instead of in successive planes. Additionally, this translational degree of freedom can be arranged at an oblique angle to the other rotational motorized degrees of freedom, so as to improve the kinematics of milling and so that the milling tool does not interfere with the bone surface. The use of inverse kinematics models are known and commonly used in robotics to control the milling path. Alternatively, more flexible control schemes can also be used such as the ACROBOT control scheme referenced above.

Figure 16:
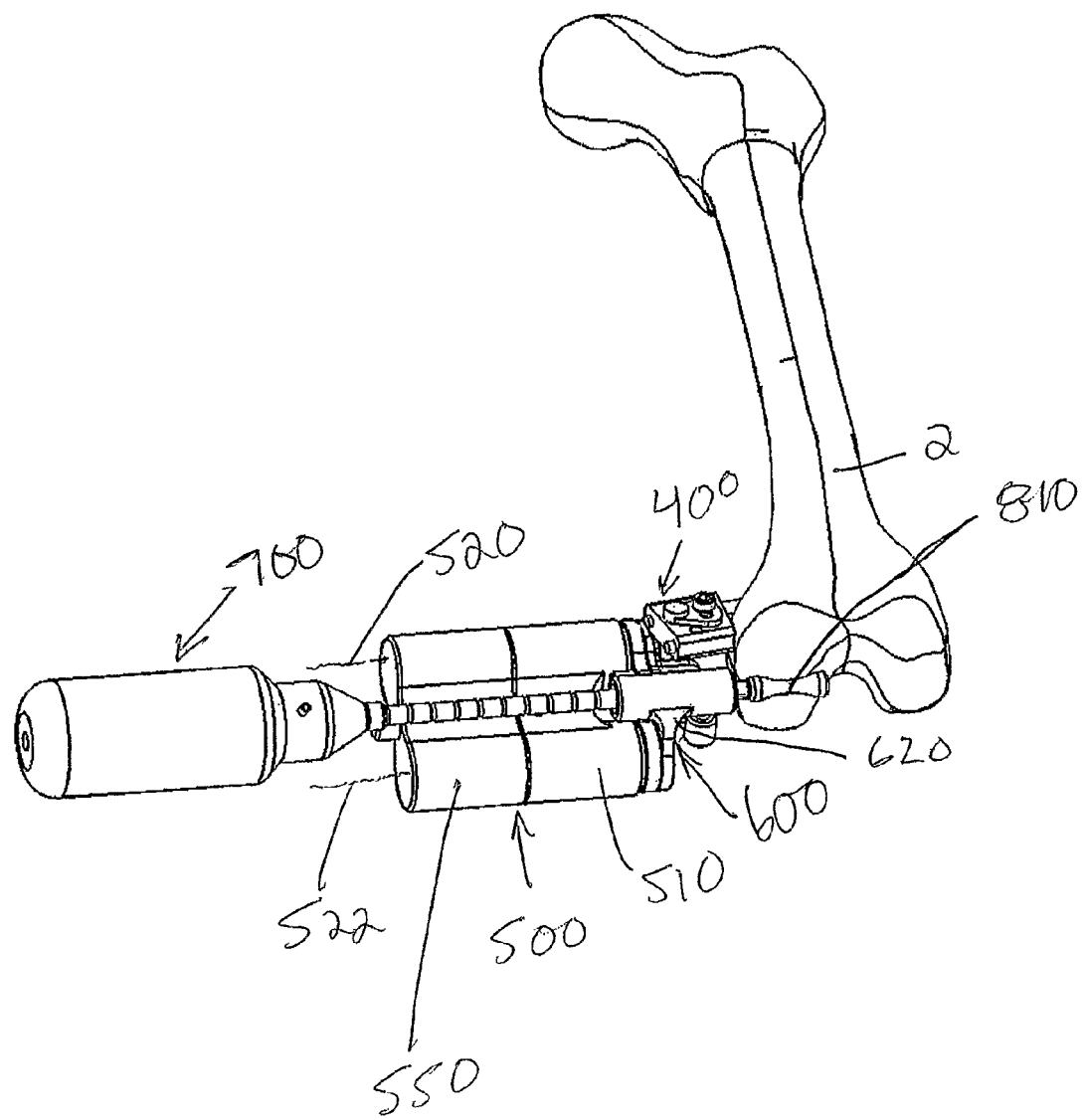
FIG. 16 is a perspective view of the milling system and guide system, with the milling system milling with a curved side cutter that conforms to the curved inner shape of the implant.

In FIG. 16, a milling device 700 has a curved side cutter 810 (curved profile) is illustrated and can be used to create a cut surface that matches precisely the shape of the implant. For example, this type of curved side cutter 810 is particularly suitable for use in uni-condylar knee arthroplasty. In this application, the motors 550 can be used to guide the trajectory during cutting for milling of complex shapes, such as curves with variable radii. It will be appreciated that the tool guide 620 allows positioning and locking of the milling tool 700 in the medial-lateral direction to center the implant.

Figure 17:
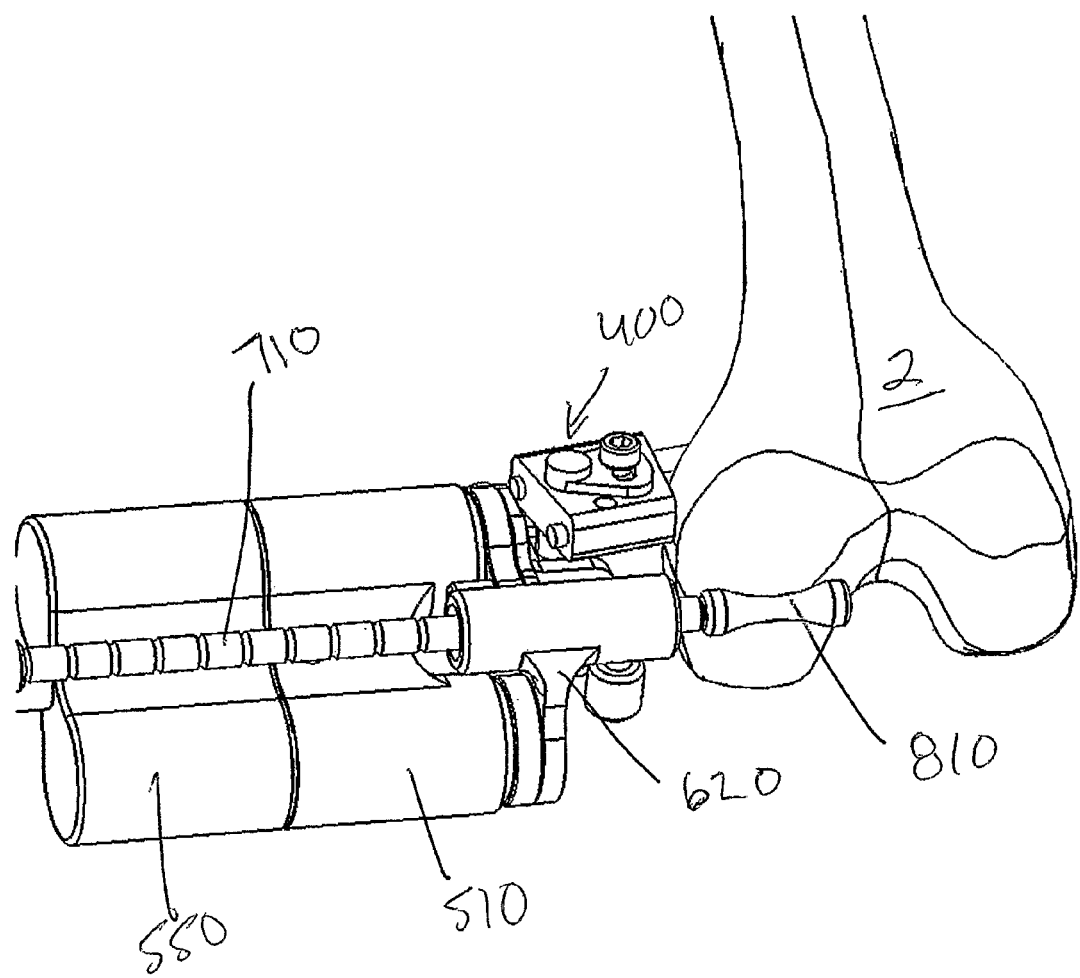
FIG. 17 is a close-up perspective of the system of FIG. 16.

Milling cutters with inward curving implants can be used to machine shapes approximating the original shape of the bone surface to minimize the amount of bone being removed. FIG. 17 is a close-up of a section of FIG. 16.

Figure 18:
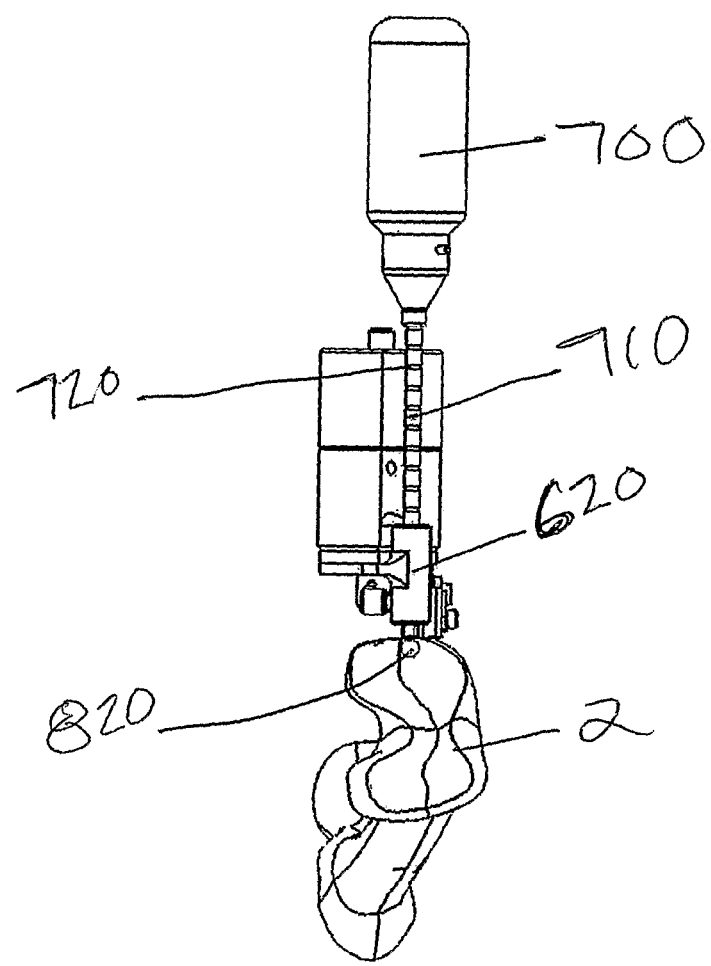
FIG. 18 is a perspective view of the milling system milling with a ball end cutter.

Alternatively and as shown in FIG. 18, a curved cutter 820 that only partially corresponds to the inner implant surface can be used. One exemplary curved cutter 820 is a ball-shaped cutter. Here, straight or curved cutting trajectories are machined into successive planes that can be perpendicular to the two motor axes 520, 522 (FIG. 3). The surgeon can manually advance and lock the milling device 700 to the next plane after the cut on the previous plane is finished, by using the indexing system (notches 720) or by using graduated markings on the milling attachment piece 620 (graduated marker system) or the navigation system 100 to advance the cutting tool 700. The computer system 120 can be used to control the positioning system 500 so as to adjust the milling trajectory as a function of the contour plane level as measure by the navigation system. In this embodiment, the notches 720 can be closer together to obtain a better surface. The bone 2 can be arranged so that the center of gravity is in line with the fixation assembly 300 so as to minimize the moment acting on the fixation pins 310 due to the weight of the system 100.

In another embodiment, the system can be used in an end-milling configuration, so that the axis of the milling tool is substantially perpendicular to the cutting surface. The axis of the milling tool can be arranged such that is perpendicular to the axes of rotation 520, 522. This could be particularly useful for cutting curvilinear surfaces, such as those commonly used in unicompartmental knee arthroplasty.

In any of the above embodiments the position of the cutting tool with respect to the bone surface can be displayed in real time. In particular the milling tool can be displayed with respect the boundary of the cut, so that the surgeon known where they are cutting with respect to the edge of the bone, and can pay particular attention so as not to exit outside this boundary in certain zones and injure soft tissues. In particular this boundary can be displayed in different colors, for example, to distinguish areas in which the model is more accurate then others. Accuracy can be estimated by the number of points acquired in the region. Known dangerous zones can also be highlighted, for example where vessels or nerves typically are found.

The present system 100 provides a number of advantages. Using at least one of the following: (1) the identified landmark points; (2) the locations of the joints; (3) the relative bone positions; and (4) the three dimensional shapes of the involved bones, the system 100 can determine an optimal implant position relative to the bone coordinate system 170. The following is merely a list of additional features that can be incorporated into the system 100 according to the present invention: using probe 160 to navigate and check the location of two fixations pins 310 and the anchor element 320 with respect to planned cuts to make sure they do not intersect any cutting surfaces; a femoral rigid body can be installed at the base of the orienting apparatus 400 to avoid having to install additional pins in the bone 2 to fix the rigid body; calibrating the axis of the milling tool 700 and the diameter of its tip; tracking the milling tool 700 with respect to the bone 2 and displaying the milling tool 700 relative to the bone 2 and in particular, relative to the boundaries of the cut; controlling the milling tool speed as a function of the tool position in the bone; providing a soft tissue guide on the milling tool 700; incorporating an irrigation system in the tool 700 for spraying out of the cutter bearing; and calibration systems for calibrating the location of the robotic member; the angular index values of the motors 550; and controlling the position of the motors 550 to align the cutting guide to the implant plan. The present system 100 also provides improved visibility by using only one, slender cutting interface for all of the planar cuts in TKA; it provides a system for positioning the saw-blade guide 610 at the start of the posterior and anterior cuts; it provided an indexed milling tool 700 in which depth advancement of the cutting tool (mechanically optionally) permits the efficient machining and decoupling of the freedom; and it provides a passive cutting guide that allows the surgeon to move a milling tool with a combination of at least one rotation and one translation degree of freedom.

The system 100 can also be configured to measure the motion of one bone in space, and to identify the centers of adjacent joints from the measured trajectories. Furthermore, the system 100 can be configured to measure the motion of one bone relative to another for various arcs of joint motion and degrees of joint rotation. An IM bone plug can be made from bioabsorbable materials and can be left in the bone. These bioabsorbable materials can contain antibiotic type materials to prevent infection, particularly in revision surgery. It can also serve as a cement restrictor to prevent the cement from entering the intramedullary canal.

The following example illustrates the use of the system 100 of the present invention in a typical surgical procedure.

EXAMPLE

Figure 21:
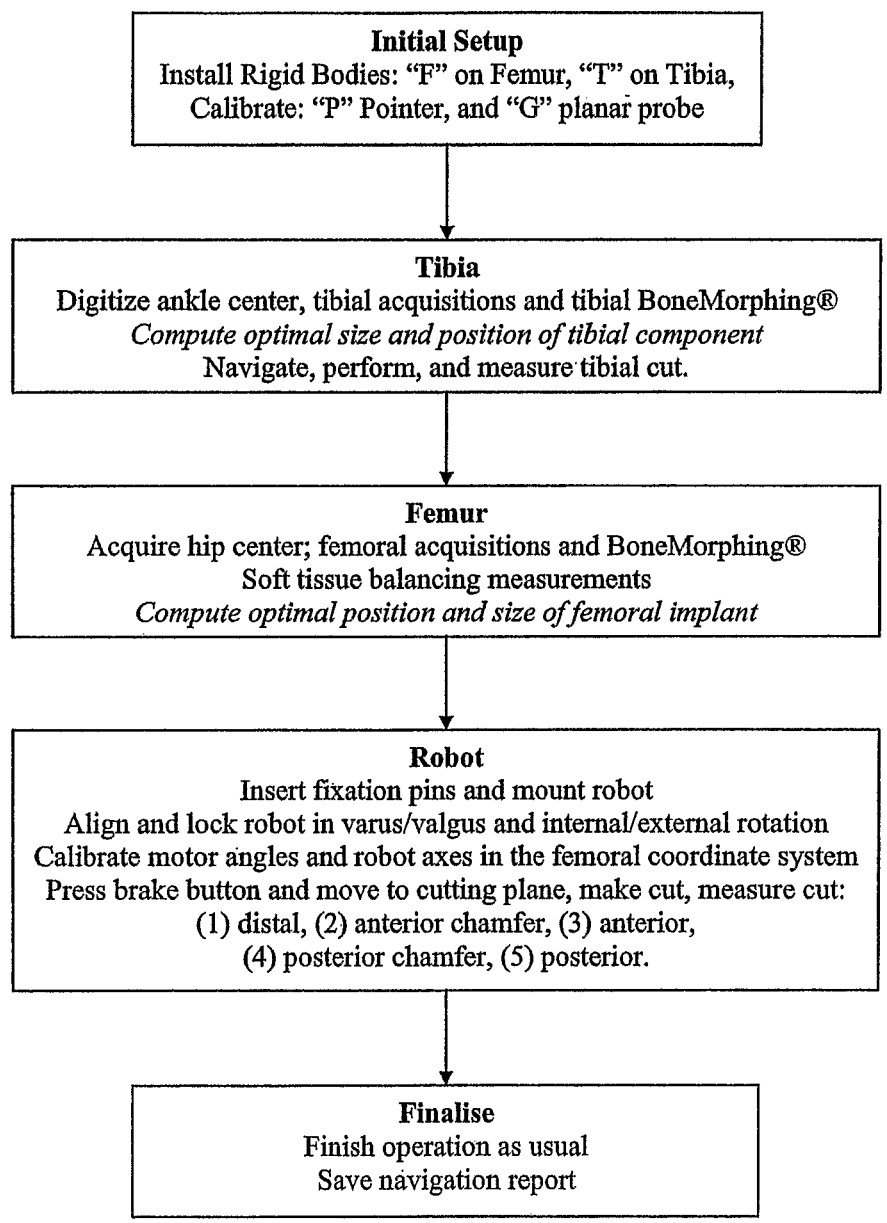
FIG. 21 is a flow chart of an exemplary surgical procedure using the guide system of the present invention in a joint replacement (TKA) operation.

Referring to FIG. 21, the robotic cutting guide of the present invention was integrated into the Surgetics Station®, distributed by the present assignee, which is an open platform surgical navigation system that uses image-free BoneMorphing® (deformable statistical) models to reconstruct the three-dimensional shape of the femoral and tibial surface intra-operatively.

The surgical workflow is present in FIG. 21. With reference to FIGS. 2 and 21, first, the T and F rigid bodies 150, 140 are fixed to the tibia 4 and the femur 2, respectively, and the point probe "P" and planar guide probe "G" are calibrated. These rigid bodies and probes each have at least three passive retroreflective markers that are localized in three-dimensional space by an optical infrared camera.

To access the knee joint, a medial parapatellar approach with a skin incision length of about 9.5 cm, which is approximately two times the length of the patella. The incision is continued down through the anterior joint capsule and patellofemoral ligament. A 2 cm snip in the vastus medialis in the direction of the fibers facilitates the exposure along with resection of the tibial meniscus and cruciate ligaments.

The tibial maleoli are first digitized to compute the ankle center, followed by the tibial plateaus. These data determine the initial attitude of the BoneMorphing model. The tibial surface acquisitions are then made by manipulating the tibia with respect to the femur in flexion, extension and rotation to help bring the various bone areas into the incision. The patella was not reflected by retracted or subluxed laterally. A conventional tibial cutting guide was then navigated and secured to the anterior tibial surface with two pins. The tibial cut was made with an oscillating saw, and the final cut surface was measured with the planar "G" probe.

The femoral acquisition begins with kinematic identification of the hip center without any rigid bodies in the pelvis. The posterior condyles and Whiteside's line are then digitized followed by the femoral BoneMorphing surface acquisition. Again, the tibia is flexed, extended, and rotated relative to the femur to expose the different femoral surface areas. There is now more space in the knee as the tibial plateau has already been removed; the tibia can be compressed against the femur and the patella can be distracted laterally. A curved probe facilitates acquisition of the posterior femoral areas with the knee in flexion, and the lateral areas with the knee in extension. Once the surface acquisition is complete, ligament gasp measurements between the uncut femoral condyles and the tibial cut surface can be performed at various flexion angles to optimize femoral component positioning and sizing. The system then automatically suggests the optimal position and the size of the femoral implant based on the mechanical axis, the bony landmark features extracted from the BoneMorphing model, and the ligament balancing acquisitions. This proposition can then be checked and modified using the tactile display screen of the computer. Once the femoral implant size and position have been validated, the locations of the five cutting planes are stored in the femoral coordinate system.

The robot fixation pins are then installed in the medial femoral condyle using a guide to help keep the pins parallel and separated by the appropriate distance. To assure that the pins do not intersect any of the five cutting planes, each cutting plane location, along with the position and orientation of the "P" probe, are displayed in real time on the navigation screen. The insertion site of the medial collateral ligament along with the planned insertion points of the two fixation pins can be marked on the bone surface to facilitate the insertion. The pin insertion area on the medial side of the femur is bounded by the following structures: anterodistally—by the anterior and anterior chamfer cuts; distally—by the distal cutting plane; posteriorly—by the anterior border of the medial collateral ligament when the knee is in full extension; anterosuperiorly—by the posteroinferior border of the vastus medialis muscle when the knee is in flexion. Fixing the robot in this area permitted uninhibited flexion and extension of the knee, and access to all five cuts through the mobile incision.

4 mm diameter, self tapping fixation pins were used without drilling any pilot holes. The bone quality and density of the fresh cadaver specimen we tested was relatively good, resulting in a rigid and very satisfactory fixation. We are planning a study to assess the rigidity of the two pin configuration in severely osteoporotic bone, however, to see whether or not this fixation technique is appropriate for all patients.

The gear unit with the pre-attached mechanical adjustment system and cutting tool guide are then mounted onto the fixation pins. With the calibrated planar probe ("G" rigid body) inserted in the slot of the guide, robot axis is aligned in varus/valgus and internal/external rotation using the numerical values displayed on the navigation screen. Each degree of freedom can be navigated and locked separately for ease-of-use. Once the adjustments are aligned relative to the planned implant profile, the motor unit is attached and the two kinematic axes and motor angles of the robot are calibrated. This is accomplished by pressing the brake release button on the 2 DOF gear unit, and manually rotating the first robot axis through a range of motion of ~90°. Simultaneous measurement of the motor encoder values and of the "G" rigid body locations with respect to the "F" femoral reference frame are made using the motion controller and the optical camera, respectively.

Using a simple inverse kinematic model that considers the geometry of the robot and the mill or saw-guide, and the position of each cutting plane relative to the robot kinematic axes and encoder calibration constants, the system computes which motor command values correspond to each of the five cutting planes. At this point the robot motors are enabled and the guide can be advanced to the first cut by pressing the system foot pedal and the robot brake release button. The footswitch sends a command to the motion controller to initiate motion of the motors, and the controller monitors the encoder values, notifying the surgeon to engage the mechanical brake once the guide is in position. In addition, the planar guide probe can be inserted in the mill or saw-guide slot to verify the guide position before making a cut.

One preferred cutting order is (1) distal, (2) anterior chamfer, (3) anterior, (4) posterior chamfer, (5) posterior. The distal cut was chosen first in our surgical protocol because it allows the surgeon to visually gauge overall varus/valgus and internal/external rotational alignment, as well as distal cutting depth, before making any of the femoral bone cuts. The anterior chamfer cut was made next followed by the anterior cut so that the cutting guide can be positioned directly against the start of the cut for both cuts, which is an improvement over most over conventional 4-in-1 and 5-in-1 types of cutting guides$_{(3)}$. This becomes more important when using an oscillating saw, as cutting accuracy is known to diminish with extension of the saw-blade beyond the cutting guide. Moreover, making the anterior cuts before the posterior ones could free more space in the joint for making the posterior cut, which is more difficult due to the position of the tibia and the delicate soft tissues behind the knee. Although this is one preferred sequence, the cutting order is not rigid and can be changed to suit surgeon preference. This is quickly and easily accomplished by using the forward or back switches on the system foot pedal to cycle through the cutting sequence. After performing a resection, the accuracy of each cut can be verified using the planar probe. These values are stored into the digital surgical report at the end of the surgery.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different points set forth below may be combined in various ways in further accordance with the present invention.

What is claimed is:

1. A system for guiding a cutting tool capable of cutting portions of a bone, comprising:
    a fixation assembly having a fastener for attaching the system to a side of the bone;
    an adjustment mechanism that includes:
        a base for fixedly attaching to the fixation assembly, and
        a mount pivotably attached to the base about a first axis and a second axis transverse to the first axis;
    a positioning mechanism that includes:
        a first arm having a first rotational axis, wherein the first arm is mounted to and rotatably coupled to the mount,
        a second arm having a second rotational axis substantially parallel to the first rotational axis,
        a motor configured to rotate at least one of the first and second arms about the respective first and second rotational axes, and
        a housing, wherein the first arm, the second arm, and the motor are housed within the housing; and
    a guide rotatably coupled to the second arm of the positioning mechanism and rotatable relative to the positioning mechanism about the second rotational axis spaced a fixed distance from the first rotational axis at all rotational positions of the positioning mechanism relative to the adjustment mechanism,
    wherein actuation of the motor causes the rotation of the at least one of the first and second arms to adjust a position of the guide relative to the adjustment mechanism.

2. The system of claim 1, wherein the fastener comprises an anchor element configured to be fixedly inserted into the bone and at least one fixation pin that is configured to pass through the bone and coupled to the anchor element by being received through a through hole formed therein.

3. The system of claim 2, wherein the anchor element is an elongated substantially hollow member, with the through hole formed in a side thereof, the fixation pin being an elongated member that is received in the through hole.

4. The system of claim 2, wherein the fastener further comprises a second guide that is detachably coupled to the anchor element and includes at least one guide through hole that is axially aligned with the through hole in the anchor element so as to guide the fixation pin through the bone and into the through hole formed in the anchor element, wherein the second guide includes a base that is configured to be disposed outside and along one side of the bone and an arm that is detachably coupled to the anchor element, the base including the at least one guide through hole.

5. The system of claim 1, wherein rotation of the positioning mechanism relative to the adjustment mechanism changes the position of the guide in a sagittal plane of the bone.

6. The system of claim 5, wherein the positioning mechanism further includes a gear unit detachably coupled to the motor, and wherein the motor includes a pair of actuators to cause rotation of the first and second arms about respective rotational axes of the positioning mechanism to cause movement of the positioning mechanism relative to the adjustment mechanism and movement of the guide relative to the positioning mechanism.

7. The system of claim 1, wherein the positioning mechanism includes a brake mechanism that prevents rotation of the positioning mechanism relative to the adjustment mechanism upon actuation.

8. The system of claim 7, wherein the brake mechanism comprises a spring-loaded manual brake mechanism with an interface element, the brake mechanism being actuated by manipulation of the interface element.

9. The system of claim 1, wherein the guide comprises a saw-blade guide including a slot for receiving the cutting tool in the form of a saw-blade, wherein the guide includes a linear sliding joint in a plane of the cut so that the saw-blade guide can be slid closer to or further away from the bone.

10. The system of claim 1, wherein the guide comprises a milling guide that is rotatably mounted to the positioning mechanism to guide the cutting tool which is in the form of a milling tool.

11. The system of claim 10, wherein the milling guide is configured for making planar cuts and includes at least one rotational degree of freedom and at least one translational degree of freedom in a cutting plane.

12. The system of claim 11, wherein an axis of the translational degree of freedom is at least substantially parallel to an axis of rotation of the milling tool, wherein an axis of the milling tool intersects at right angles the rotational degree of freedom of the milling guide.

13. The system of claim 10, wherein the milling tool guide includes a slot formed therein for guiding a saw-blade so as to permit the milling tool to be used for some cuts and the saw-blade to be used for making other cuts.

14. The system of claim 10, wherein the milling guide and the milling tool have an indexing system incorporated therein and constructed such that the milling tool is configured to be discretely advanced into the cut after each cutting swing of the cutting tool.

15. The system of claim 14, wherein an interface between a milling tool attachment piece and a translational joint of the milling guide is indexed so as to allow the milling tool to be advanced in discrete intervals, the indexing being in the form of a series of circumferential grooves formed in the outer surface of the milling tool attachment piece.

16. The system of claim 10, wherein the milling guide and the milling tool are configured to permit machining of non-planar cut surfaces.

17. A system for guiding a cutting tool capable of cutting bone comprising:
    a fixation assembly having a fastener for attaching the system to a bone;
    an adjustment mechanism that includes:
        a base removeably coupled to the fixation assembly, and
        a mount pivotably attached to the base about two rotational degrees of freedom traversing one another;
    a positioning mechanism that includes:

a first arm rotatably coupled to the mount of the adjustment mechanism, the first arm having a first longitudinal rotational axis, a second arm spaced from the first arm, the second arm having a second longitudinal rotational axis substantially parallel to and spaced a fixed distance from the first longitudinal rotational axis, and a motor configured to rotate at least one of the first arm and the second arm about the respective first and second longitudinal rotational axes, wherein the first arm, the second arm and the motor are housed within a housing of the positioning mechanism; and a guide coupled to the second arm of the positioning mechanism about a sliding joint, wherein actuation of the motor causes the rotation of the at least one of the first and second arms to adjust a position of the guide relative to the adjustment mechanism.

18. The system of claim 17, wherein the adjustment mechanism is coupled to the fixation assembly by a sliding joint.

19. The system of claim 17, wherein the fixation assembly includes an anchor element having a through hole for receiving the fastener therethrough.

20. The system of claim 17, wherein the positioning mechanism has a proximal end and a distal end, and wherein the adjustment mechanism and the guide are each rotatably coupled to the proximal end of the positioning mechanism.

21. A system for guiding a cutting tool comprising:
a fixation assembly having a fastener for attaching the system to bone;
an adjustment mechanism that includes:
a base fixedly attachable to the fixation assembly, and
a mount pivotally attached to the base about two rotational degrees of freedom traversing one another;
a positioning mechanism that includes:
a first arm rotatably coupled to the mount and including a first longitudinal rotational axis,
a second arm spaced from the first arm and including a second longitudinal axis substantially parallel to and spaced a fixed distance from the first longitudinal rotational axis, and
a motor configured to move at least one of the first arm and the second arm about respective first and second longitudinal axes, wherein the first arm, the second arm the and the motor are housed within a housing of the positioning mechanism; and
a guide coupled to the second arm of the positioning mechanism about a pivot joint,
wherein actuation of the motor causes the movement of the at least one of the first and second arms to adjust a position of the guide relative to the adjustment mechanism.

22. The system of claim 21, wherein the positioning mechanism has a proximal end and a distal end, and wherein the fixation assembly and the guide are each rotatably coupled to the proximal end of the positioning mechanism.

23. The system of claim 21, wherein the fastener comprises an anchor element configured to be fixedly inserted into the bone and at least one fixation pin configured to pass through the bone and coupled to the anchor element by being received through a through hole formed therein.

24. The system of claim 21, wherein the fixation assembly is configured to attach the system to a medial side of the bone.

25. The system of claim 21, wherein the guide includes a slot for receiving the cutting tool in the form of a saw-blade.

26. The system of claim 21, wherein the guide include a pair of spaced apart planar members forming a slot for receiving the cutting tool.

27. The system of claim 21, wherein rotation of the positioning mechanism relative to the fixation assembly changes the position of the guide in a sagittal plane of the bone.

28. The system of claim 17, wherein the fixation assembly is configured to attach the system to a medial side of the bone.

29. The system of claim 17, wherein the fastener comprises a pair of pins or screws.

30. The system of claim 29, wherein the pair of pins or screws directly attaches to the adjustment mechanism.

31. A system for guiding a cutting tool capable of cutting portions of a bone, comprising:
a fixation assembly comprising a fixation fastener for attaching the system to a side of the bone;
an adjustment mechanism that includes:
a base for fixedly attaching to the fixation assembly, and
a mount pivotally attached to the base about two rotational degrees of freedom traversing one another;
a motorized positioning mechanism that includes:
a housing,
a first arm rotatably mounted within the housing, wherein the first arm includes a first longitudinal rotational axis and is rotatably coupled to the mount,
a second arm rotatably mounted within the housing and spaced a fixed distance from the first arm, wherein the second arm includes a second longitudinal rotational axis substantially parallel to the first longitudinal rotational axis, and
a brake mechanism housed within the housing, the brake mechanism comprising a spring loaded brake, a mechanical brake or an electromechanical brake configured to prevent rotation of the first and second arms relative to the housing upon actuation; and
a guide rotatably coupled to the second arm of the positioning mechanism and rotatable relative to the positioning mechanism about the second longitudinal rotational axis,
wherein actuation of the motorized positioning mechanism adjusts a position of the guide relative to the adjustment mechanism.

\* \* \* \* \*